(12) United States Patent
Callan et al.

(10) Patent No.: US 11,712,473 B2
(45) Date of Patent: Aug. 1, 2023

(54) SENSITIZER-PEPTIDE CONJUGATE

(71) Applicant: UNIVERSITY OF ULSTER, Coleraine (GB)

(72) Inventors: John Francis Callan, Ballycastle (GB); Bridgeen Callan, Ballycastle (GB); Anthony Patrick McHale, Ballycastle (GB)

(73) Assignee: UNIVERSITY OF ULSTER, County Londonderry (GB)

( * ) Notice: Subject to any disclaimer, the term of this patent is extended or adjusted under 35 U.S.C. 154(b) by 0 days.

(21) Appl. No.: 16/625,664

(22) PCT Filed: Jun. 25, 2018

(86) PCT No.: PCT/EP2018/066982
§ 371 (c)(1),
(2) Date: Dec. 20, 2019

(87) PCT Pub. No.: WO2018/234586
PCT Pub. Date: Dec. 27, 2018

(65) Prior Publication Data
US 2021/0154297 A1 May 27, 2021

(30) Foreign Application Priority Data
Jun. 23, 2017 (GB) .................................. 1710097

(51) Int. Cl.
*A61K 41/00* (2020.01)
*C07K 7/06* (2006.01)

(52) U.S. Cl.
CPC ...... *A61K 41/0057* (2013.01); *A61K 41/0033* (2013.01); *C07K 7/06* (2013.01)

(58) Field of Classification Search
CPC ............ A61K 41/0033; A61K 41/0057; A61K 41/0071; A61K 49/0056; C07K 5/1019; C07K 7/06; C07K 7/08
See application file for complete search history.

(56) References Cited

U.S. PATENT DOCUMENTS

| | | | | |
|---|---|---|---|---|
| 10,588,972 | B2 * | 3/2020 | Kovar | A61K 47/6415 |
| 11,071,781 | B2 * | 7/2021 | Wachter | A61K 38/193 |
| 2007/0219134 | A1 * | 9/2007 | Ruoslahti | C07K 5/1019 514/1.2 |
| 2008/0003200 | A1 * | 1/2008 | Arap | A61K 47/64 514/1.2 |
| 2010/0184681 | A1 * | 7/2010 | Eckert | A61K 47/64 530/387.3 |

FOREIGN PATENT DOCUMENTS

| | | |
|---|---|---|
| KR | 101 493 168 B1 | 2/2015 |
| WO | 2003/079966 A2 | 10/2003 |
| WO | 2008/039994 A2 | 4/2008 |
| WO | 2017/034482 A2 | 3/2017 |
| WO | 2018/234586 A1 | 12/2018 |

OTHER PUBLICATIONS

Costley et al. Sonodynamic inactivation of Gram-positive and Gram-negative bacteria using a Rose Bengal-antimicrobial peptide conjugate. In J Antimicr Agents,vol. 49, pp. 31-36 (Year: 2017).*
Liu et al. Mechanistic Studies of a Peptidic GRP78 Ligand for Cancer Cell-Specific Drug Delivery. Mol Pharmaceutics, vol. 4, No. 3, pp. 435-447 (Year: 2007).*
Dhillon et al. Rose Bengal-Amphiphilic Peptide Conjugate for Enhanced Photodynamic Therapy of Malignant Melanoma. J. Med. Chem. 2020, 63, 3, pp. 1328-1336. (Year: 2020).*
Inaba et al., "Ultrasound-dependent cytoplasmic internalization of peptide-sonosensitizer conjugate," Elsevier, ScienceDirect, Bioorganic & Medicinal Chemistry; 25; pp. 4212-4217; Jun. 15, 2017.
Johnson et al., "Photoinduced Membrane Damage of E. coli and S. aureus by the Photosensitizer-Antimicrobial Peptide Conjugate Eosin-(KLAKLAK)2," PLOS One; vol. 9, No. 3; pp. 1-14; Mar. 7, 2014.
Johnson et al., "Photoinactivation of Gram Positive and Gram Negative Bacteria with the Antimicrobial Peptide (KLAKLAK)2 Conjugated to the Hydrophilic Photosensitizer Eosin Y," Bioconjugate Chemistry; vol. 24, No. 1; pp. 114-123; Dec. 17, 2012.
Mukai et al., "The synthesis of 64Cu-chelated porphyrin photosensitizers and their tumor-targeting peptide conjugates for the evaluation of target cell uptake and PET image-based pharmacokinetics of targeted photodynamic therapy agents," Ann. Nucl. Med.; DOI 10.1007/s12149-013-0728-2; vol. 27; pp. 625-639; Apr. 20, 2013.
Schneider et al., "Recent Improvements in the Use of Synthetic Peptides for a Selective Photodynamic Therapy," Anti-Cancer Agents in Medicinal Chemistry; vol. 6, No. 5; pp. 469-488; Sep. 1, 2006.
Tirand et al., "Metabolic Profile of a Peptide-Conjugated Chlorin-Type Photosensitizer Targeting Neuropilin-1: An in Vivo and in Vitro Study," Drug Metabolism and Disposition, vol. 35, No. 5; pp. 806-813; May 1, 2007.
PCT International Search Report and Written Opinion for International Application No. PCT/EP2018/066982 entitled "A Sensitizer-Peptide Conjugate," dated Oct. 4, 2018; Consisting of 15 pages.

* cited by examiner

*Primary Examiner* — Marcela M Cordero Garcia
(74) *Attorney, Agent, or Firm* — Hamilton, Brook, Smith & Reynolds, P.C.

(57) ABSTRACT

The present invention relates to a sensitizer-peptide conjugate for use in the treatment of cancer. In particular, the present invention relates to a sensitizer-peptide conjugate for use in the treatment of melanoma. The use of such sensitizer-peptide conjugate in photodynamic therapy or sonodynamic therapy is also disclosed. According to the present invention, there is provided a sensitizer-peptide conjugate for use in the treatment of cancer; wherein the sensitizer-peptide conjugate comprises at least one sensitizer and at least one peptide.

13 Claims, 11 Drawing Sheets
Specification includes a Sequence Listing.

SEQUENCE LISTING

<160> NUMBER OF SEQ ID NOS: 6

<210> SEQ ID NO 1
<211> LENGTH: 14
<212> TYPE: PRT
<213> ORGANISM: Unknown
<220> FEATURE:
<223> OTHER INFORMATION: Synthetic peptide

<400> SEQUENCE: 1

Lys Leu Ala Lys Leu Ala Lys Lys Leu Ala Lys Leu Ala Lys
1               5                   10

```
<210> SEQ ID NO 2
<211> LENGTH: 15
<212> TYPE: PRT
<213> ORGANISM: Unknown
<220> FEATURE:
<223> OTHER INFORMATION: Synthetic peptide

<400> SEQUENCE: 2

Cys Lys Leu Ala Lys Leu Ala Lys Lys Leu Ala Lys Leu Ala Lys
1               5                   10                  15

<210> SEQ ID NO 3
<211> LENGTH: 4
<212> TYPE: PRT
<213> ORGANISM: Unknown
<220> FEATURE:
<223> OTHER INFORMATION: Synthetic peptide

<400> SEQUENCE: 3

Lys Leu Ala Lys
1

<210> SEQ ID NO 4
<211> LENGTH: 29
<212> TYPE: PRT
<213> ORGANISM: Unknown
<220> FEATURE:
<223> OTHER INFORMATION: Synthetic peptide

<400> SEQUENCE: 4

Cys Lys Leu Ala Lys Leu Ala Lys Lys Leu Ala Lys Leu Ala Lys Lys
1               5                   10                  15

Leu Ala Lys Leu Ala Lys Lys Leu Ala Lys Leu Ala Lys
            20                  25

<210> SEQ ID NO 5
<211> LENGTH: 7
<212> TYPE: PRT
<213> ORGANISM: Unknown
<220> FEATURE:
<223> OTHER INFORMATION: Synthetic peptide

<400> SEQUENCE: 5

Lys Leu Ala Lys Leu Ala Lys
1               5

<210> SEQ ID NO 6
<211> LENGTH: 8
<212> TYPE: PRT
<213> ORGANISM: Unknown
<220> FEATURE:
<223> OTHER INFORMATION: Synthetic peptide

<400> SEQUENCE: 6

Cys Lys Leu Ala Lys Leu Ala Lys
1               5
```

SENSITIZER-PEPTIDE CONJUGATE

RELATED APPLICATIONS

This application is the U.S. National Stage of International Application No. PCT/EP2018/066982, filed on Jun. 25, 2018, which designates the United States of America, published in English, and claims priority under 35 U.S.C. § 119 or 365(c) to Great Britain Application No. 1710097.5, filed on Jun. 23, 2017. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 57691000002_SequenceListing; created Dec. 20, 2019, 2 KB in size.

FIELD OF THE INVENTION

The present invention relates to a sensitizer-peptide conjugate for use in the treatment of cancer. In particular, the present invention relates to a sensitizer-peptide conjugate for use in the treatment of melanoma. The use of such a sensitizer-peptide conjugate in photodynamic therapy or sonodynamic therapy of cancer is also disclosed.

BACKGROUND OF THE INVENTION

Melanoma is an aggressive form of cancer with current treatment involving radical surgical excision, chemotherapy, and/or radiotherapy. In the metastatic disease state, systemic therapy using expensive immunotherapy drugs (e.g. pembrolizumab, costing approximately GBP 90,000 per patient annually) or conventional chemotherapeutics (e.g. decarbazine) are the most common treatments. In 2008, skin cancer collectively cost the United Kingdom (UK) National Health Service (NHS) an estimated GBP106-112 million. In 2014, there were 15,419 cases of melanoma, which caused 2,469 deaths, ranking as the fifth most common cancer in the UK. Incidence rates for melanoma are predicted to grow approximately 7% in the UK from 2014 to 2035, resulting in 32 cases per 100,000 people. Melanoma is notoriously resistant to chemotherapeutics. Decarbazine, the NICE approved chemotherapeutic for melanoma, achieves patient remission in only 5-10% of cases.

Photodynamic therapy (PDT) is currently approved as a first line treatment for non-melanoma skin cancer and has been trialled in the treatment of other cancers such as head and neck, oesophageal, bladder, and prostate cancer. PDT is based on the presence of three distinct components: (i) a photosensitizer (e.g. a sensitising drug), (ii) light of an appropriate wavelength, and (iii) molecular oxygen. These agents are non-toxic alone but, when the photosensitizer absorbs the light of an appropriate wavelength, the excited triplet state interacts with molecular oxygen by electron (Type I) or energy (Type II) transfer processes that result in the generation of singlet oxygen and other reactive oxygen species (ROS) such as superoxide, hydrogen peroxide, and hydroxyl that, when generated in sufficient quantities, results in cell death. The attraction of PDT over other cancer therapies is that generation of the cytotoxic species can be controlled by careful positioning of the illumination source. Control of the ROS generation via the light stimulus results in a precisely focused treatment, which can be within <0.02 µM of the focal point. Moreover, PDT is beneficial in reducing the occurrence of tumour resistance as multiple forms of ROS are produced simultaneously. Another advantage of PDT is the excellent cosmetic outcome observed post treatment when compared to surgery or topical chemotherapy treatment (e.g. 5-fluorouracil). However, because of the high reactivity and short half-life (0.04 µs) of singlet oxygen, the diffusion radius can be less than 20 nm; meaning only cells close to the site of singlet oxygen generation are affected. Moreover, the limited penetration of light through mammalian tissue has restricted the use of PDT to the treatment of superficial lesions and reduces the effectiveness of PDT in treating more deeply-seated or highly-pigmented lesions. Indeed, while PDT is routinely used to treat superficial basal cell carcinoma (BCC), it is not indicated for the treatment of malignant melanoma. The dark pigmentation associated with melanotic lesions acts as a filter for the light used to activate the majority of conventional sensitizers that absorb in the visible range of the electromagnetic spectrum.

In recent years it has been demonstrated that many of the existing clinically-used photosensitizers can be 'activated' by ultrasound, although the precise mechanism(s) by which this occurs remain(s) unknown. Such sonodynamic therapy (SDT) has recently emerged as an alternative to PDT and uses low intensity ultrasound instead of light to activate the sensitizer. This interaction of the sensitizer with an acoustic field generates ROS that result in cytotoxic effects similar to those observed in PDT. A major benefit of using SDT instead of PDT is that, unlike light, ultrasound can achieve penetration depths in soft tissue in the region of tens of centimetres. Therefore, SDT offers the potential of treating more deeply seated solid tumours than currently possible using PDT.

There remains a need for improved treatment options for cancer, in particular pigmented cancers such as melanoma.

SUMMARY OF THE INVENTION

According to a first aspect of the present invention, there is provided a sensitizer-peptide conjugate for use in the treatment of cancer; wherein the sensitizer-peptide conjugate comprises at least one sensitizer and at least one peptide.

Optionally, the at least one peptide comprises at least part of the amino acid sequence KLAKLAK (SEQ ID NO:5). Further optionally, the at least one peptide comprises the amino acid sequence KLAKLAK (SEQ ID NO:5). Still further optionally, the at least one peptide consists of the amino acid sequence KLAKLAK (SEQ ID NO:5).

Optionally, the at least one peptide comprises at least part of the amino acid sequence defined by SEQ ID NO:5. Further optionally, the at least one peptide comprises the amino acid sequence defined by SEQ ID NO:5. Still further optionally, the at least one peptide consists of the amino acid sequence defined by SEQ ID NO:5.

Optionally, the at least one peptide comprises at least part of the amino acid sequence CKLAKLAK (SEQ ID NO:6). Further optionally, the at least one peptide comprises the amino acid sequence CKLAKLAK (SEQ ID NO:6). Still further optionally, the at least one peptide consists of the amino acid sequence CKLAKLAK (SEQ ID NO:6).

Optionally, the at least one peptide comprises at least part of the amino acid sequence SEQ ID NO:6. Further optionally, the at least one peptide comprises the amino acid sequence SEQ ID NO:6. Still further optionally, the at least one one peptide consists of the amino acid sequence SEQ ID NO:6.

Optionally, the at least one peptide comprises at least part of the amino acid sequence KLAKLAKKLAKLAK (SEQ ID NO: 1). Further optionally, the at least one peptide comprises the amino acid sequence KLAKLAKKLAKLAK (SEQ ID NO: 1). Still further optionally, the at least one peptide consists of the amino acid sequence KLAK-LAKKLAKLAK (SEQ ID NO: 1).

Optionally, the at least one peptide comprises at least part of the amino acid sequence defined by SEQ ID NO: 1. Further optionally, the at least one peptide comprises the amino acid sequence defined by SEQ ID NO: 1. Still further optionally, the at least one peptide consists of the amino acid sequence defined by SEQ ID NO: 1.

Optionally, the at least one peptide comprises at least part of the amino acid sequence CKLAKLAKKLAKLAK (SEQ ID NO: 2). Further optionally, the at least one peptide comprises the amino acid sequence CKLAKLAKKLAK-LAK (SEQ ID NO: 2). Still further optionally, the at least one peptide consists of the amino acid sequence CKLAK-LAKKLAKLAK (SEQ ID NO: 2).

Optionally, the at least one peptide comprises at least part of the amino acid sequence defined by SEQ ID NO: 2. Further optionally, the at least one peptide comprises the amino acid sequence defined by SEQ ID NO: 2. Still further optionally, the at least one peptide consists of the amino acid sequence defined by SEQ ID NO: 2.

Optionally, the at least one peptide comprises at least part of the amino acid sequence KLAK (SEQ ID NO: 3). Further optionally, the at least one peptide comprises the amino acid sequence KLAK (SEQ ID NO: 3). Still further optionally, the at least one peptide consists of the amino acid sequence KLAK (SEQ ID NO: 3).

Optionally, the at least one peptide comprises at least part of the amino acid sequence defined by SEQ ID NO: 3. Further optionally, the at least one peptide comprises the amino acid sequence defined by SEQ ID NO: 3. Still further optionally, the at least one peptide consists of the amino acid sequence defined by SEQ ID NO: 3.

Optionally, the at least one peptide comprises at least part of the amino acid sequence CKLAKLAKKLAK-LAKKLAKLAKKLAKLAK (SEQ ID NO: 4). Further optionally, the at least one peptide comprises the amino acid sequence CKLAKLAKKLAKLAKKLAKLAKKLAKLAK (SEQ ID NO: 4). Still further optionally, the at least one peptide consists of the amino acid sequence CKLAK-LAKKLAKLAKKLAKLAKKLAKLAK (SEQ ID NO: 4).

Optionally, the at least one peptide comprises at least part of the amino acid sequence defined by SEQ ID NO: 4. Further optionally, the at least one peptide comprises the amino acid sequence defined by SEQ ID NO: 4. Still further optionally, the at least one peptide consists of the amino acid sequence defined by SEQ ID NO: 4.

Optionally, the at least one peptide comprises at least part of the amino acid sequence defined by a sequence selected from the group comprising: SEQ ID NO: 1, SEQ ID NO: 2, SEQ ID NO: 3, SEQ ID NO: 4, SEQ ID NO: 5, and SEQ ID NO: 6. Further optionally, the at least one peptide comprises the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6. Still further optionally, the at least one peptide consists of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6.

Optionally, the at least one peptide further comprises at least one additional amino acid.

Further optionally, the at least one peptide comprises at least one additional amino acid at the N-terminal end of an amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6.

Optionally, the at least one peptide further comprises at least three additional amino acids. Further optionally, the at least one peptide further comprises at least three additional amino acids at the N-terminal end of an amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6.

Optionally, the at least one additional amino acid comprises at least one proteinogenic amino acid. Optionally, the at least one additional amino acid comprises at least one amino acid selected from the group comprising: a nonpolar amino acid, a polar amino acid, a hydrophobic amino acid, a neutral amino acid, a negatively charged amino acid, a positively charged amino acid, a sulphur-containing amino acid, an aliphatic amino acid, a basic amino acid, an acidic amino acid, an amide amino acid, an aromatic amino acid, a cyclic amino acid, and a hydroxyl-containing amino acid.

Optionally, the at least three additional amino acids each comprise a proteinogenic amino acid. Optionally, the at least three additional amino acids each comprise an amino acid selected from the group comprising: nonpolar amino acids, polar amino acids, hydrophobic amino acids, neutral amino acids, negatively charged amino acids, positively charged amino acids, sulphur-containing amino acids, aliphatic amino acids, basic amino acids, acidic amino acids, amide amino acids, aromatic amino acids, cyclic amino acids, and hydroxyl-containing amino acids.

Optionally, the at least one peptide further comprises at least one additional amino acid comprising a sulphur atom. Further optionally, the at least one peptide further comprises at least one additional amino acid comprising a thiol group. Still further optionally, the at least one peptide further comprises at least one additional amino acid comprising a sulphur atom at the N-terminal end of SEQ ID NO. 1. Still further optionally, the at least one peptide further comprises at least one additional amino acid comprising a thiol group at the N-terminal end of SEQ ID NO. 1.

Optionally, the at least one peptide further comprises at least one additional amino acid comprising a sulphur atom. Further optionally, the at least one peptide further comprises at least one additional amino acid comprising a thiol group. Still further optionally, the at least one peptide further comprises at least one additional amino acid comprising a sulphur atom at the N-terminal end of SEQ ID NO. 5. Still further optionally, the at least one peptide further comprises at least one additional amino acid comprising a thiol group at the N-terminal end of SEQ ID NO. 5.

Optionally or additionally, the at least one amino acid is selected from cysteine and methionine. Further optionally or additionally, the at least one amino acid is cysteine.

Optionally, the sensitizer-peptide conjugate is connectable to another entity by a thiol bond. Optionally, the sensitizer-peptide conjugate is connectable to another entity by a thiol bond by means of a Michael addition reaction. Optionally, the cysteine is connectable to another entity by a thiol bond by means of a Michael addition reaction.

Optionally, the at least one peptide comprises at least part of the amino acid sequence defined by GenBank Accession.Version Number AAB21494.1. Further optionally, the at least one peptide comprises the amino acid sequence defined by GenBank Accession.Version Number AAB21494.1. Still further optionally, the at least one peptide consists of the amino acid sequence defined by GenBank Accession.Version Number AAB21494.1.

Optionally, the at least one peptide comprises at least part of the amino acid sequence defined by GenBank reference sequence Accession.Version Number XP_003394701.1. Further optionally, the at least one peptide comprises the amino acid sequence defined by GenBank Accession.Version Number XP_003394701.1. Still further optionally, the at least one peptide consists of the amino acid sequence defined by GenBank Accession.Version Number XP_003394701.1.

Optionally, the at least one peptide comprises at least part of the amino acid sequence defined by GenBank Accession.Version Number NP_001011617.1. Further optionally, the at least one peptide comprises the amino acid sequence defined by GenBank Accession.Version Number NP_001011617.1. Still further optionally, the at least one peptide consists of the amino acid sequence defined by GenBank Accession.Version Number NP_001011617.1.

Optionally, the at least one peptide comprises at least part of the amino acid sequence defined by GenBank Accession.Version Number ACH96383.1. Further optionally, the at least one peptide comprises the amino acid sequence defined by GenBank Accession.Version Number ACH96383.1. Still further optionally, the at least one peptide consists of the amino acid sequence defined by GenBank Accession.Version Number ACH96383.1.

Optionally, the at least one peptide comprises at least part of the amino acid sequence defined by GenBank Accession.Version Number AAB33924.1. Further optionally, the at least one peptide comprises the amino acid sequence defined by GenBank Accession.Version Number AAB33924.1. Still further optionally, the at least one peptide consists of the amino acid sequence defined by GenBank Accession.Version Number AAB33924.1.

Optionally, the at least one peptide comprises an amino acid sequence that has at least 95% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 90% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 85% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 80% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 75% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 70% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 60% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 50% identity with the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises an amino acid sequence that has at least 95% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 90% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 85% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 80% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 75% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 70% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 60% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1. Optionally, the at least one peptide comprises an amino acid sequence that has at least 50% identity with at least part of the amino acid sequence defined by a sequence selected from the group comprising: SEQ ID NO. 1, SEQ ID NO. 2, SEQ ID NO. 3, SEQ ID NO. 4, SEQ ID NO: 5, and SEQ ID NO: 6; or any GenBank Accession.Version Number selected from the group comprising: AAB21494.1, XP_003394701.1, NP_001011617.1, ACH96383.1, and AAB33924.1.

Optionally, the at least one peptide comprises at least part of the amino acid sequence defined by any GenBank Accession.Version Number selected from the group comprising: AAB21494.1, XP_003394701.1, NP_001011617.1, ACH96383.1, and AAB33924.1. Further optionally, the at least one peptide comprises the amino acid sequence defined by any GenBank Accession.Version Number selected from the group comprising: AAB21494.1, XP_003394701.1, NP_001011617.1, ACH96383.1, and AAB33924.1. Still further optionally, the at least one peptide consists of the amino acid sequence defined by any GenBank Accession.Version Number selected from the group comprising: AAB21494.1, XP_003394701.1, NP_001011617.1, ACH96383.1, and AAB33924.1.

Optionally, the at least one sensitizer comprises a compound selected from the group comprising: photosensitizers, photosensitizer precursors, photosensitizer derivatives, sonosensitizers, sonosensitizer precursors, and sonosensitizer derivatives.

Optionally, the at least one sensitizer comprises a compound selected from the group comprising: photosensitizers, photosensitizer precursors, photosensitizer derivatives, photosensitizers suitable for use in PDT, photosensitizer precursors suitable for use in PDT, photosensitizer derivatives suitable for use in PDT, sonosensitizers, sonosensitizer precursors, sonosensitizer derivatives, sonosensitizers suitable for use in SDT, sonosensitizer precursors suitable for use in SDT, and sonosensitizer derivatives suitable for use in SDT.

Optionally, the at least one sensitizer comprises a compound selected from the group comprising: porphyrins, chlorins, and dyes. Optionally, the at least one sensitizer comprises a compound selected from the group comprising: porphyrin precursors, chlorin precursors, and dye precursors. Optionally, the at least one sensitizer comprises a compound selected from the group comprising: porphyrin derivatives, chlorin derivatives, and dye derivatives.

Optionally, the at least one sensitizer comprises a dye.

Optionally, the at least one sensitizer comprises phthalocyanine. Optionally, the at least one sensitizer comprises a phthalocyanine derivative. Optionally, the at least one sensitizer comprises an aluminium phthalocyanine. Optionally, the at least on sensitizer comprises a sulphonated aluminium phthalocyanine. Optionally, the at least one sensitizer comprises a compound selected from the group comprising: aluminium phthalocyanine disulphonate ($AlPcS_2$), aluminium phthalocyanine disulphonate with the sulfonate groups on adjacent rings ($AlPcS_{2a}$), and aluminium phthalocyanine tetra-sulfonate ($AlPcS_4$).

Optionally, the at least one sensitizer comprises chlorin. Optionally, the at least one sensitizer comprises a chlorin derivative. Optionally, the at least one sensitizer comprises a compound selected from the group comprising: tetra(m-hydroxyphenyl)chlorin (m-THPC), temoporfin, mono-L-aspartyl chlorin e6 (NPe6), and chlorin e6.

Optionally, the at least one sensitizer comprises bacteriochlorin. Optionally, the at least one sensitizer comprises a bacteriochlorin derivative. Optionally, the at least one sensitizer comprises ketochlorin. Optionally, the at least one sensitizer comprises a ketochlorin derivative.

Optionally, the at least one sensitizer comprises porphyrin. Optionally, the at least one sensitizer comprises a porphyrin derivative.

Optionally, the at least one sensitizer comprises hematoporphyrin. Optionally, the at least one sensitizer comprises a hematoporphyrin derivative. Optionally, the at least one sensitizer comprises benzoporphyrin. Optionally, the at least one sensitizer comprises a benzoporphyrin derivative. Optionally, the at least one sensitizer comprises a compound selected from the group comprising: protoporphyrin IX (PpIX); indocyanine green (ICG), ICG iodinated derivatives; IR-783 (2-[2-[2-Chloro-3-[2-[1,3-dihydro-3,3-dimethyl-1-(4-sulfobutyl)-2H-indol-2-ylidene]ethylidene]-1-cyclohexen-1-yl]-ethenyl]-3,3-dimethyl-1-(4-sulfobutyl)-3H-indolium hydroxide), iodinated derivatives of IR-783; 5-aminolevulinic acid (5-ALA; 5-amino-4-oxo-pentanoic acid), and derivatives of 5-ALA.

Optionally, the at least one sensitizer comprises tetraphenylporphyrin (TPP). Optionally, the at least one sensitizer comprises a sulphonated tetraphenylporphyrin. Optionally, the at least one sensitizer comprises a compound selected from the group comprising: tetraphenylporphyrin monosulphonate ($TPPS_1$), tetraphenylporphine disulphonate with the sulfonate groups on adjacent rings ($TPPS_{2a}$), tetraphenylporphine disulphonate with the sulfonate groups on opposite rings ($TPPS_{2o}$), tetraphenylporphyrin tetra-sulphonate ($TPPS_4$).

Optionally, the at least one sensitizer comprises fluorescein. Optionally, the at least one sensitizer comprises a fluorescein derivative.

Optionally, the at least one sensitizer comprises Rose Bengal. Optionally, the at least one sensitizer is Rose Bengal (4,5,6,7-tetrachloro-2',4',5',7'-tetraiodofluorescein).

Optionally, the at least one sensitizer comprises a Rose Bengal derivative.

Optionally, the at least one sensitizer comprises a photosensitizer selected from the group comprising: Rose Bengal, Eosin, Eosin Y (2-(2,4,5,7-tetrabromo-6-oxido-3-oxo-3H-xanthen-9-yl)benzoate), and Eosin B (4',5'-dibromo-3',6'-dihydroxy-2',7-dinitro-1-spiro[isobenzofuran-3,9'-xanthene]one).

Optionally, the sensitizer-peptide conjugate comprises Rose Bengal and a peptide comprising at least part of the amino acid sequence defined by SEQ ID NO: 5. Further optionally, the sensitizer-peptide conjugate comprises Rose Bengal and a peptide comprising the amino acid sequence defined by SEQ ID NO: 5. Optionally, the sensitizer-peptide conjugate comprises Rose Bengal and a peptide consisting of the amino acid sequence defined by SEQ ID NO: 5.

Optionally, the sensitizer-peptide conjugate comprises Rose Bengal and a peptide comprising at least part of the amino acid sequence defined by SEQ ID NO: 6. Further optionally, the sensitizer-peptide conjugate comprises Rose Bengal and a peptide comprising the amino acid sequence defined by SEQ ID NO: 6. Optionally, the sensitizer-peptide conjugate comprises Rose Bengal and a peptide consisting of the amino acid sequence defined by SEQ ID NO: 6.

Optionally, the sensitizer-peptide conjugate comprises Rose Bengal and a peptide comprising at least part of the amino acid sequence defined by SEQ ID NO: 1. Further optionally, the sensitizer-peptide conjugate comprises Rose Bengal and a peptide comprising the amino acid sequence defined by SEQ ID NO: 1. Optionally, the sensitizer-peptide conjugate comprises Rose Bengal and a peptide consisting of the amino acid sequence defined by SEQ ID NO: 1.

Optionally, the sensitizer-peptide conjugate comprises Rose Bengal and a peptide comprising at least part of the amino acid sequence defined by SEQ ID NO: 2. Further optionally, the sensitizer-peptide conjugate comprises Rose Bengal and a peptide comprising the amino acid sequence defined by SEQ ID NO: 2. Optionally, the sensitizer-peptide conjugate comprises Rose Bengal and a peptide consisting of the amino acid sequence defined by SEQ ID NO: 2.

Optionally, the sensitizer-peptide conjugate further comprises at least one linker. Further optionally, the sensitizer-peptide conjugate further comprises at least one linker between the at least one sensitizer and the at least one peptide.

Optionally, the at least one sensitizer comprises a carboxylic acid functional group. Further optionally, the sensitizer-peptide conjugate further comprises at least one linker connected to the carboxylic acid functional group of the at least one sensitizer.

Optionally, the at least one linker comprises one or more chemical bonds selected from the group comprising: an ionic bond, a covalent bond, a metallic bond, a hydrogen bond, dipole-dipole interactions, and Van der Waals forces.

Optionally, the at least one linker comprises one or more polymers.

Optionally, the at least one linker comprises one or more organic functional groups.

Optionally, the at least one linker comprises at least one amino acid. Optionally, the at least one linker comprises at least three amino acids.

Optionally, the at least one linker comprises at least one organic functional group connected to at least one amino acid.

Optionally, the at least one organic functional group is selected from the group comprising: a hydrocarbon chain, an alkane, an alkene, an alkyne, an ester, a ketone, an ether, an amine, an amide, an alcohol, a halogen, an aldehyde, and a carboxylic acid.

Optionally, the at least one linker comprises a ketone. Further optionally, the at least one linker comprises a ketone selected from propanone, butanone, pentanone, hexanone, heptanone, octanone, nonanone, and decanone.

Optionally, the at least one linker comprises a carboxylic acid. Further optionally, the at least one linker comprises a hydrocarbon chain selected from propane, butane, pentane, hexane, heptane, octane, nonane, and decane. Further optionally, the at least one linker comprises a carboxylic acid selected from the group comprising: propanoic acid, butanoic acid, pentanoic acid, hexanoic acid, heptanoic acid, octanoic acid, nonanoic acid.

Optionally, the at least one linker comprises heptane.

Optionally, the at least one linker comprises octane. Further optionally, the at least one linker comprises octanoic acid (caprylic acid).

Optionally, the at least one linker comprises the general formula

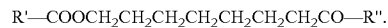

R'—COOCH$_2$CH$_2$CH$_2$CH$_2$CH$_2$CH$_2$CO—R".

Optionally, the at least one linker comprises at least one amino acid is selected from the group comprising: cysteine, and methionine.

Optionally, the sensitizer-peptide conjugate is connectable to another entity by a thiol bond. Optionally, the sensitizer-peptide conjugate is connectable to another entity by a thiol bond by means of a Michael addition reaction. Optionally, the linker is connectable to another entity by a thiol bond, optionally by means of a Michael addition reaction. Optionally, the cysteine is connectable to another entity by a thiol bond, optionally by means of a Michael addition reaction.

Optionally, the sensitizer-peptide conjugate comprises Rose Bengal, at least one linker, and a peptide comprising at least part of the amino acid sequence defined by SEQ ID NO: 5. Further optionally, the sensitizer-peptide conjugate comprises Rose Bengal, an octane linker, and a peptide comprising at least part of the amino acid sequence defined by SEQ ID NO: 5. Still further optionally, the sensitizer-peptide conjugate comprises Rose Bengal, a linker comprising the general formula COOCH$_2$CH$_2$CH$_2$CH$_2$CH$_2$CH$_2$CO, and a peptide comprising at least part of the amino acid sequence defined by SEQ ID NO: 5.

Optionally, the sensitizer-peptide conjugate comprises Rose Bengal, at least one linker, and a peptide comprising at least part of the amino acid sequence defined by SEQ ID NO: 6. Further optionally, the sensitizer-peptide conjugate comprises Rose Bengal, an octane linker, and a peptide comprising at least part of the amino acid sequence defined by SEQ ID NO: 6. Still further optionally, the sensitizer-peptide conjugate comprises Rose Bengal, a linker comprising the general formula COOCH$_2$CH$_2$CH$_2$CH$_2$CH$_2$CH$_2$CO, and a peptide comprising at least part of the amino acid sequence defined by SEQ ID NO: 6.

Optionally, the sensitizer-peptide conjugate comprises Rose Bengal, at least one linker, and a peptide comprising at least part of the amino acid sequence defined by SEQ ID NO: 1. Further optionally, the sensitizer-peptide conjugate comprises Rose Bengal, an octane linker, and a peptide comprising at least part of the amino acid sequence defined by SEQ ID NO: 1. Still further optionally, the sensitizer-peptide conjugate comprises Rose Bengal, a linker comprising the general formula COOCH$_2$CH$_2$CH$_2$CH$_2$CH$_2$CH$_2$CO, and a peptide comprising at least part of the amino acid sequence defined by SEQ ID NO: 1.

Optionally, the sensitizer-peptide conjugate comprises Rose Bengal, at least one linker, and a peptide comprising at least part of the amino acid sequence defined by SEQ ID NO: 2. Further optionally, the sensitizer-peptide conjugate comprises Rose Bengal, an octane linker, and a peptide comprising at least part of the amino acid sequence defined by SEQ ID NO: 2. Still further optionally, the sensitizer-peptide conjugate comprises Rose Bengal, a linker comprising the general formula $COOCH_2CH_2CH_2CH_2CH_2CH_2CH_2CO$, and a peptide comprising at least part of the amino acid sequence defined by SEQ ID NO: 2.

Optionally, the sensitizer-peptide conjugate is the D enantiomer.

Optionally, the sensitizer-peptide conjugate is the R enantiomer.

Optionally, the sensitizer-peptide conjugate comprises both the D enantiomer and the R enantiomer.

Optionally, the sensitizer-peptide conjugate comprises a racemate. Alternatively, the sensitizer-peptide conjugate is enantiomerically pure.

Optionally, the peptide comprises at least one D enantiomer amino acid. Optionally, the peptide comprises chiral amino acids, wherein a proportion of the chiral amino acids are D enantiomers. Optionally, the peptide comprises chiral amino acids, wherein at least a proportion of the chiral amino acids are D enantiomers. Optionally, the proportion is selected from the range 50%-100%. Optionally, the proportion is selected from the group comprising: about 50%, about 60%, about 70%, about 80%, about 90%, and about 100%.

Optionally, the peptide comprises at least one chiral amino acid, wherein the at least one chiral amino acid is the D enantiomer.

Optionally, the peptide comprises at least one L enantiomer amino acid. Optionally, the peptide comprises chiral amino acids, wherein a proportion of the chiral amino acids are L enantiomers. Optionally, the peptide comprises chiral amino acids, wherein at least a proportion of the chiral amino acids are L enantiomers. Optionally, the proportion is selected from the range 50%-100%. Optionally, the proportion is selected from the group comprising: about 50%, about 60%, about 70%, about 80%, about 90%, and about 100%.

Optionally, the peptide comprises at least one chiral amino acid, wherein the at least one chiral amino acid is the L enantiomer.

Optionally, the sensitizer-peptide conjugate is activated by a trigger, optionally leading to the generation of reactive oxygen species; optionally singlet oxygen.

Optionally, the use is part of photodynamic therapy.

Optionally, the trigger is light. Optionally, the trigger is selected from the group comprising visible light, and infrared light.

Optionally, the trigger is near-infrared light.

Optionally, the trigger is visible light selected from the group comprising: white light, red light, orange light, yellow light, green light, blue light, and violet light.

Optionally, the trigger is electromagnetic radiation. Optionally the trigger is electromagnetic radiation having a wavelength of 380 nm to 950 nm.

Optionally, the use is part of sonodynamic therapy.

Optionally, the trigger is sound. Optionally, the trigger is ultrasound.

Optionally, the trigger is sound having a frequency of at least 20 kiloHertz.

Optionally, the cancer is a malignant neoplasm.

Optionally, the cancer is a solid tumour cancer. Optionally, the cancer is a liquid tumour cancer.

Optionally, the cancer is skin cancer. Optionally, the cancer is basal cell carcinoma.

Optionally, the cancer is selected from the group comprising: breast cancer, pancreatic cancer, skin cancer, head and neck cancer, oesophageal cancer, bladder cancer, and prostate cancer.

Optionally, the cancer is pigmented.

Optionally the cancer is melanoma.

Optionally, the sensitizer-peptide conjugate is activated by exposure to the trigger for a duration of up to about 30 minutes. Optionally, the sensitizer-peptide conjugate is activated by exposure to the trigger for a duration selected from the group comprising: about 1 second, about 5 seconds, about 10 seconds, about 20 seconds, about 25 seconds, about 30 seconds, about 35 seconds, about 40 seconds, about 50 seconds, about 55 seconds, about 60 seconds, about 1 minute, about 2 minutes, about 3 minutes, about 30 minutes.

Also disclosed is the use of a sensitizer-peptide conjugate in the manufacture of a medicament for the treatment of cancer.

Optionally, the sensitizer-peptide conjugate is a sensitizer-peptide conjugate according to the first aspect of the present invention.

Optionally, the trigger is a trigger according to the first aspect of the present invention.

Optionally, the cancer is a cancer according to the first aspect of the present invention.

According to a second aspect of the present invention, there is provided a method for the treatment of cancer comprising the steps of:
(a) providing a sensitizer-peptide conjugate comprising at least one sensitizer and at least one peptide;
(b) administering the sensitizer-peptide conjugate to the patient;
(c) administering a trigger to the patient;

Optionally, the sensitizer-peptide conjugate is a sensitizer-peptide conjugate according to the first aspect of the present invention.

Optionally, the trigger is a trigger according to the first aspect of the present invention.

Optionally, the cancer is a cancer according to the first aspect of the present invention.

Any known sensitizer (or sensitizer precursor, or sensitizer derivative), or photosensitizer (or photosensitizer precursor, or photosensitizer derivative) suitable for use in PDT or SDT may be employed in the invention. Examples of suitable photosensitizers and precursors and derivatives thereof include the following: phthalocyanines such as aluminium phthalocyanines which optionally may be sulphonated (i.e. AlPcS), e.g. di-sulphonated aluminium phthalocyanines such as $AlPcS_2$ or $AlPcS_{2a}$, or aluminium phthalocyanine tetra-sulfonate ($AlPcS_4$); sulphonated tetraphenylporphyrins (e.g. $TPPS_{2a}$, $TPPS_4$, $TPPS_1$ and $TPPS_{2o}$); chlorins such as tetra(m-hydroxyphenyl)chlorins (m-THPC) (e.g. temoporfin); chlorin derivatives including bacteriochlorins and ketochlorins; mono-L-aspartyl chlorin e6 (NPe6) or chlorin e6; porphyrins including hematoporphyrin and benzoporphyrins; protoporphyrin IX (PpIX); indocyanine green (ICG) and ICG iodinated derivatives; IR-783 and iodinated derivatives of IR-783; 5 aminolevulinic acid (5 ALA) and derivatives of 5-ALA (leading to production of protoporphyrin IX).

An aspect of the present invention also relates to a sensitizer-peptide conjugate comprising at least one sensitizer and at least one peptide as disclosed for use in the maintenance of cell homeostasis. The disclosed sensitizer-peptide conjugate can be used to maintain cell homeostasis by reducing cell proliferation (e.g. cytostatic cellular effects) or by increasing cell death (e.g. cytotoxic cellular effects). In certain embodiments, the disclosed sensitizer-peptide conjugate can be used to maintain native cell homeostasis by reducing native cell proliferation (e.g. cytostatic cellular effects) or by increasing native cell death (e.g. cytotoxic cellular effects). In certain embodiments, the disclosed sensitizer-peptide conjugate can be used to maintain native of foreign cell homeostasis by eradicating native or foreign cells (e.g. cytotoxic cellular effects). In certain embodiments, the disclosed sensitizer-peptide conjugate can be used to maintain native cell homeostasis by eradicating diseased native cells (e.g. atherosclerotic native cells, or cancerous native cells). In certain embodiments, the disclosed sensitizer-peptide conjugate can be used to maintain native cell homeostasis by selectively eradicating native cells (e.g. to reduce native cell number or to select specific cell types)—such embodiments find utility in autologous or heterologous cell transplantation (e.g. hematopoietic cell transplantation, cardiac cell transplantation, or stem cell transplantation).

A further aspect of the present invention also relates to a sensitizer-peptide conjugate comprising at least one sensitizer and at least one peptide as disclosed, for use in combination with other cancer therapies including chemotherapy, radiotherapy, immunotherapy or any combinations thereof.

The term "sensitizer" refers to a compound or drug that may be activated by a trigger, including for example light or sound. A sensitizer may be for example a photosensitizer or a sonosensitizer.

The term "RB" refers to Rose Bengal.

The term "PDT" refers to photodynamic therapy.

The term "SDT" refers to sonodynamic therapy.

The term "functional group" refers to a specific group of atoms and/or bonds, either within a compound, or that is capable of forming part of a compound.

The term "organic functional group" refers to a specific group of atoms and/or bonds, either within an organic compound, or that is capable of forming part of an organic compound.

The term "nonpolar amino acid" refers to an amino acid having a nonpolar side chain. The term "polar amino acid" refers to an amino acid having a polar side chain. The term "neutral amino acid" refers to an amino acid having a neutral side chain charge at about pH 7.4. The term "negative amino acid" refers to an amino acid having a negatively charged side chain charge at about pH 7.4. The term "positive amino acid" refers to an amino acid having a positively charged side chain charge at about pH 7.4. The term "sulphur-containing amino acid" refers to an amino acid having at least one sulphur atom in its side chain. The term "aliphatic amino acid" refers to an amino acid having an aliphatic side chain. The term "basic amino acid" refers to an amino acid having a basic side chain. The term "acidic amino acid" refers to an amino acid having an acidic side chain. The term "amide amino acid" refers to an amino acid having at least one amine functional group in its side chain. The term "aromatic amino acid" refers to an amino acid having an aromatic side chain. The term "cyclic amino acid" refers to an amino acid having a cyclic side chain. The term "hydroxyl-containing amino acid" refers to an amino acid having at least one hydroxyl functional group in its side chain.

The term "MTT" refers to 3-(4,5-dimethylthiazol-2-yl)-2,5-diphenyltetrazolium bromide.

The term "ROS" refers to reactive oxygen species.

The term "DPBF" refers to 1,3-diphenylisobenzofuran.

The term "DMEM" refers to Dulbecco's Modified Eagle Media.

The term "RP-HPLC" refers to reverse phase high performance liquid chromatography.

BRIEF DESCRIPTION OF THE DRAWINGS

Embodiments of the present invention will now be described by way of non-limiting examples, and with reference to the accompanying drawings in which:

FIG. 2 shows charts as detailed below for each part, wherein "m/z" refers to the mass-to-charge ratio.

FIG. 4 (d) shows a bar chart representing the mean bioluminescent intensity from the three repeats of each condition expressed relative to the control. Lightest grey=light only; 2$^{nd}$ lightest grey=2.5 µM concentration; 3$^{rd}$ darkest grey=5.0 µM concentration; and black=10 µM concentration. "C(KLAKLAK)$_2$" (SEQ ID NO. 2) represents a peptide having the amino acid sequence defined by SEQ ID NO. 2. "RB" represents Rose Bengal. "RB-C(KLAKLAK)$_2$" (SEQ ID NO. 2) represents a conjugate of Rose Bengal and a peptide having the amino acid sequence defined by SEQ ID NO. 2. "+light" represents photodynamic therapy. These results show a significant reduction in bioluminescence following photodynamic therapy using a conjugate of Rose Bengal and a peptide having the amino acid sequence defined by SEQ ID NO. 2, compared to photodynamic therapy using Rose Bengal or irradiating the peptide having the amino acid sequence defined by SEQ ID NO. 2 alone with light;

EXAMPLES

Figure 1:
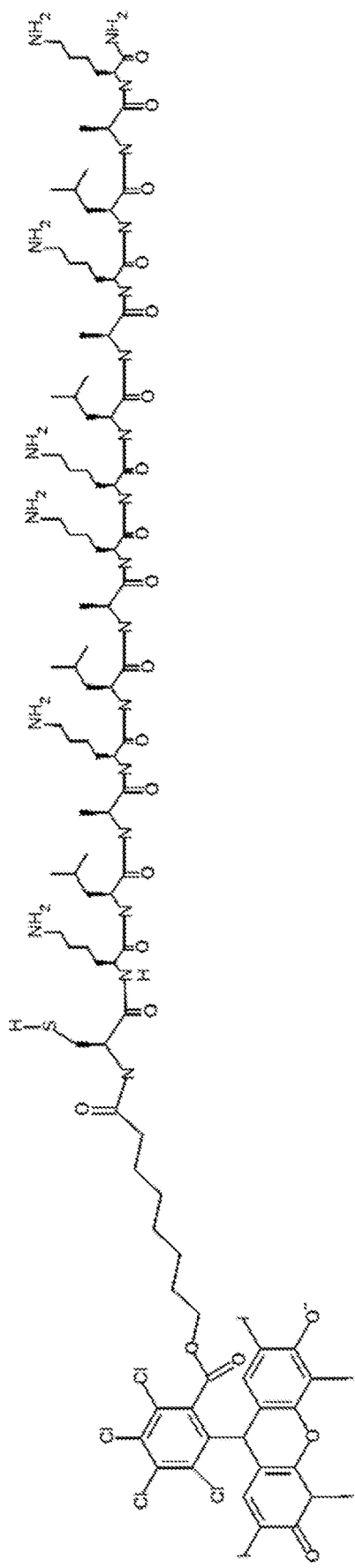
FIG. 1 is a landscape-oriented representation of the structure of a sensitizer-peptide conjugate comprising Rose Bengal and a peptide having the amino acid sequence defined by SEQ ID NO. 2.

Embodiments of the present invention will now be described with reference to the following non-limiting examples:

Materials

In respect of each example described below: Rose Bengal was purchased from Sigma-Aldrich at the highest grade possible. All other chemicals were purchased from commercial sources at the highest possible purity and used as received. The B16-F10-Luc2 cell line was purchased from PerkinElmer. SCID and athymic nude mice were obtained from Envigo.

Example 1

Preparation of Rose Bengal-C(KLAKLAK)$_2$ (SEQ ID NO. 2) and Rose Bengal-C(KLAKLAK) (SEQ ID NO. 6) Conjugates The Rose Bengal-C(KLAKLAK)$_2$ (SEQ ID NO. 2) and Rose Bengal-C(KLAKLAK) (SEQ ID NO. 6) conjugates were prepared by first synthesising the C(KLAKLAK)$_2$ (SEQ ID NO. 2) or C(KLAKLAK) (SEQ ID NO. 6) peptide using Fmoc solid phase peptide synthesis on Rink Amide resin. In parallel, a carboxylic acid derivative of Rose Bengal was also prepared by reacting Rose Bengal with 1-bromooctanoic acid following a literature procedure (Fowley C et al. 2012). This carboxylic acid derivative was added to the N-terminus of C(KLAKLAK)$_2$ (SEQ ID NO. 2) or C(KLAKLAK) (SEQ ID NO. 6) while still on the resin using standard peptide coupling reagents (i.e. HOBt/TBTU). The conjugate was then cleaved from the resin and purified using preparative reverse phase HPLC. Product formation was confirmed using MALDI-TOF and positive electrospray mass spectrometry.

RB-C(KLAKLAK)$_2$ (SEQ ID NO. 2) Conjugate: Chirality represents the structural difference between all-Levorotatory (L) and all-Dextrorotatory (D) form of RB-(KLAKLAK)$_2$ (SEQ ID NO. 1). The all-D enantiomer is postulated to be proficient in evading the body's immune-system and digestive enzymes, preventing proteolytic degradation and increasing the amount of active drug at the tumour site. Here, the all-L conjugate was modified to include an additional cysteine (C) amino acid to provide a further site of attachment via a Michael addition reaction if necessary. An all-D enantiomer RB-(KLAKLAK)$_2$ (SEQ ID NO. 1) was also prepared but did not possess cysteine functionality. The all-L enantiomer C(KLAKLAK)$_2$ (SEQ ID NO. 2) peptide i.e. minus RB was also prepared as a control.

TABLE 1

The amino-acid sequence and differences of the two enantiomers of the conjugate.

| Conjugate | In text Abbreviation | Chirality | Amino-Acid Length | Amino acid sequence | SEQ ID |
|---|---|---|---|---|---|
| RB-C(KLAKLAK)$_2$ | All-L | Levorotatory | 15 | Cys-Lys-Leu-Ala-Lys-Leu-Ala-Lys-Lys-Leu-Ala-Lys-Leu-Ala-Lys | SEQ ID NO: 2 |
| C(KLAKLAK)$_2$ | All-L | Levorotatory | 15 | Cys-Lys-Leu-Ala-Lys-Leu-Ala-Lys-Lys-Leu-Ala-Lys-Leu-Ala-Lys | SEQ ID NO: 2 |
| RB-(KLAKLAK)$_2$ | All-D | Dextrorotatory | 14 | Lys-Leu-Ala-Lys-Leu-Ala-Lys-Lys-Leu-Ala-Lys-Leu-Ala-Lys | SEQ ID NO: 1 |
| RB-C(KLAKLAK) | All-L | Levorotatory | 8 | Cys-Lys-Leu-Ala-Lys-Leu-Ala-Lys | SEQ ID NO: 6 |

Synthesis of the all-L enantiomer of Rose Bengal-C(KLAKLAK)$_2$ (SEQ ID NO. 2) conjugate: The C(KLAKLAK)$_2$ (SEQ ID NO. 2) peptide was synthesised via a standard Fmoc solid phase peptide synthesis (SPPS) procedure using Rink amide MBHA resin. Piperidine was used for Fmoc de-protection while HOBt and HBTU were used to activate the amino acids. Carboxylic acid functionalised Rose Bengal (RB-COOH) was prepared following a literature procedure (Costley et al. 2017). This was attached to the N-terminus of the peptide while on the resin to produce the conjugate. The RB-C(KLAKLAK)$_2$ (SEQ ID NO. 2) conjugate was cleaved using a TFA:water:EDT:TIPS (94:2.5:2.5:1 v/v) cleavage cocktail and the crude peptide purified using RP-HPLC (C$_{18}$ column, solvent A: 89.9% H$_2$O, 10% ACN, 0.1% TFA; solvent B: 99.9% ACN, 0.1% TFA, gradient of 75% to 2% solvent A over a period of 60 minutes). Fractions (containing the peak of interest) were combined and freeze dried to afford the desired product as a red solid.

Synthesis of the all L-enantiomer of C(KLAKLAK)$_2$ (SEQ ID NO. 2): The same procedure as described above for the synthesis of the all-L enantiomer was followed, except the peptide was cleaved from the resin before the addition of Rose Bengal. The HPLC purification conditions used were the same.

Synthesis of the all-D enantiomer of the Rose Bengal-(KLAKLAK)$_2$ (SEQ ID NO. 1) conjugate: The same procedure as described above for the synthesis of the all-L enantiomer was followed, except D-amino acids were used and the cysteine residue not included. The HPLC purification conditions were the same.

Synthesis of the all L-enantiomer of Rose Bengal-C (KLAKLAK) (SEQ ID NO. 6): The same procedure as described above for the synthesis of the all-L enantiomer was followed, except the peptide was cleaved from the resin before the addition of Rose Bengal. The HPLC purification conditions used were the same.

Example 2

Figure 2A:
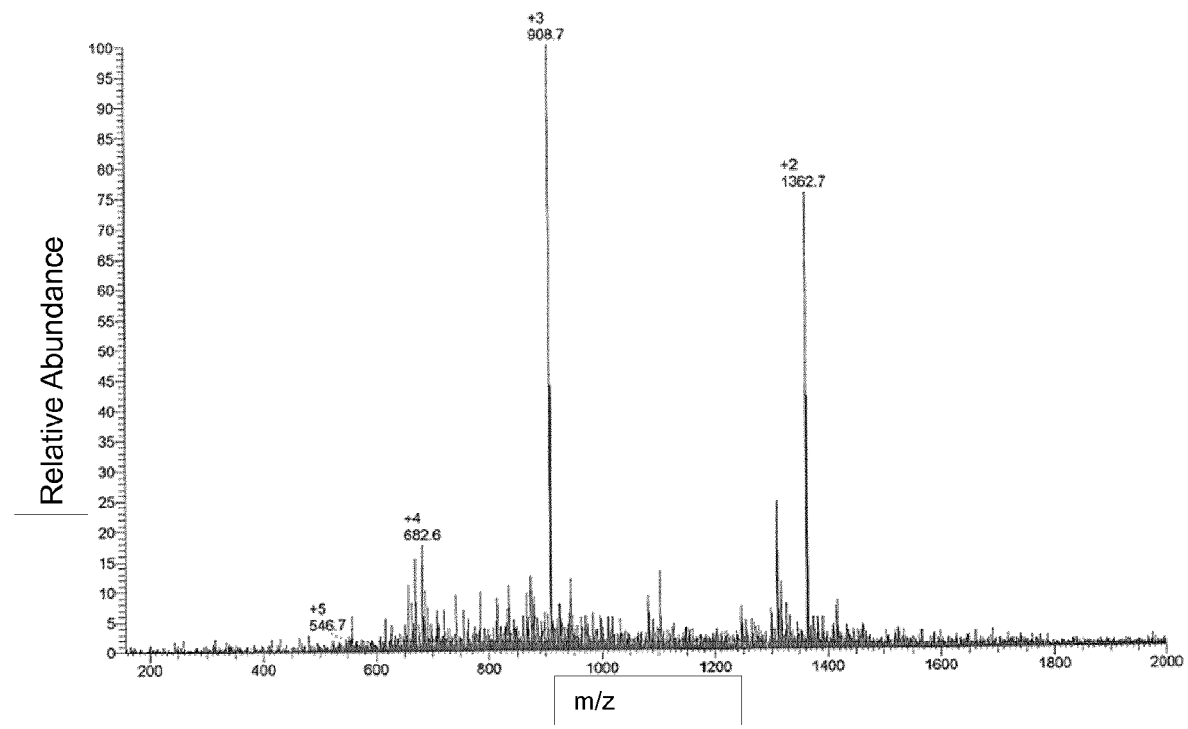
FIG. 2(a) is a chart showing a positive electrospray Mass Spectrum of all-L enantiomer of a Rose Bengal-peptide conjugate, wherein the peptide has the amino acid sequence defined by SEQ ID NO. 2. Multiple charged ions are denoted as M/2+1 and M/3+1. Calculated parent mass: 2721.2 Expected mass: 2721.6.
Figure 2B:
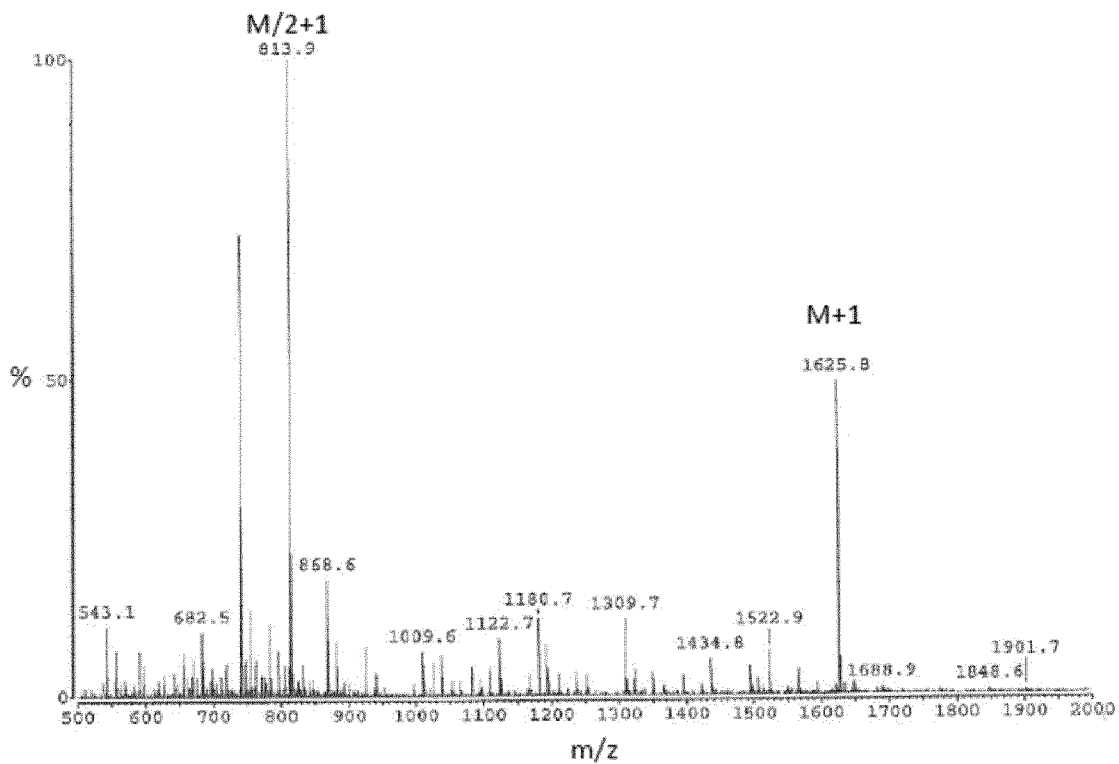
FIG. 2(b) is a chart showing a positive mode electrospray ionisation mass spectrometry (ESI-MS) Mass Spectrum of all-L enantiomer of a peptide having the amino acid sequence defined by SEQ ID NO. 2; indicating the expected M+1 m/z and associated doubly charged daughter ion (expected mass-to-charge ratio=1626.1, observed mass-to-charge ratio=1625.8).
Figure 2C:
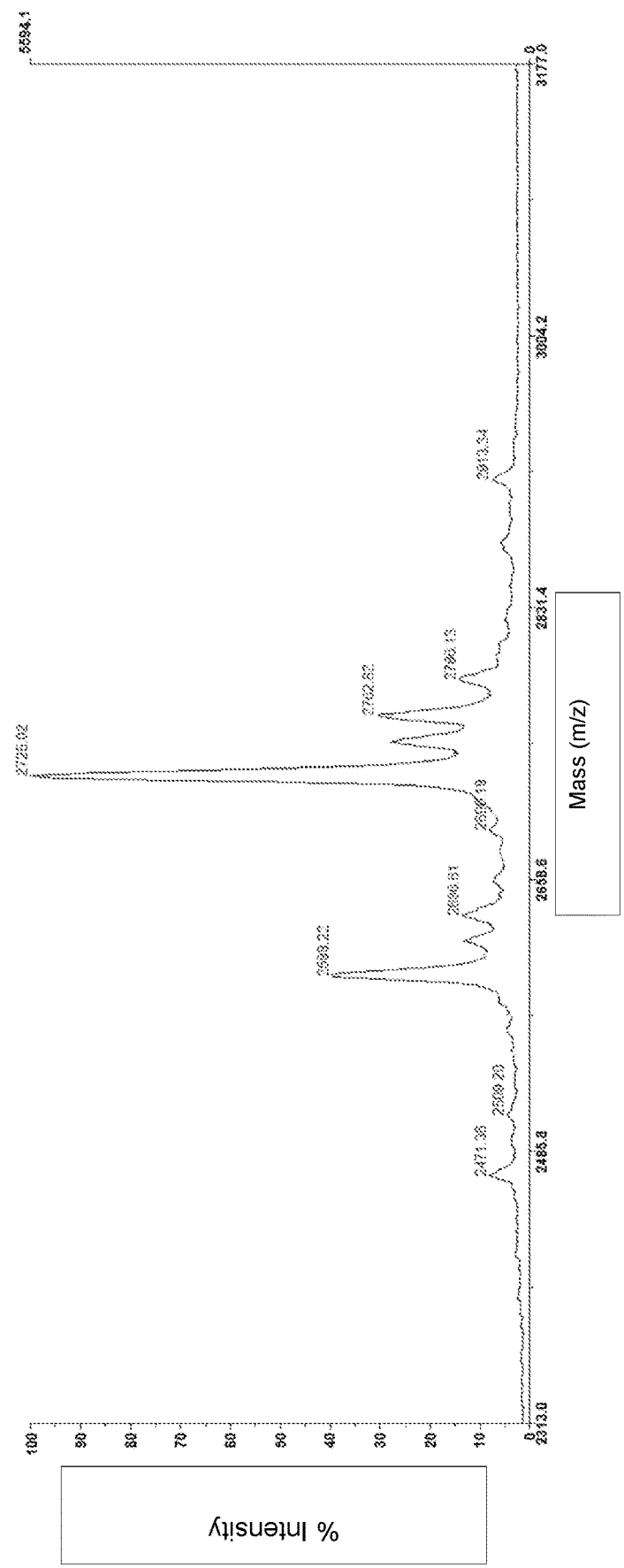
FIG. 2(c) is a landscape-oriented chart showing a Matrix Assisted Laser Desorption/ESIIonization Time-of-Flight (MALDI-TOF) spectrum of the all L-enantiomer of a Rose Bengal-peptide conjugate, wherein the peptide has the amino acid sequence defined by SEQ ID NO. 2. Expected mass: 2721.6.
Figure 2D:
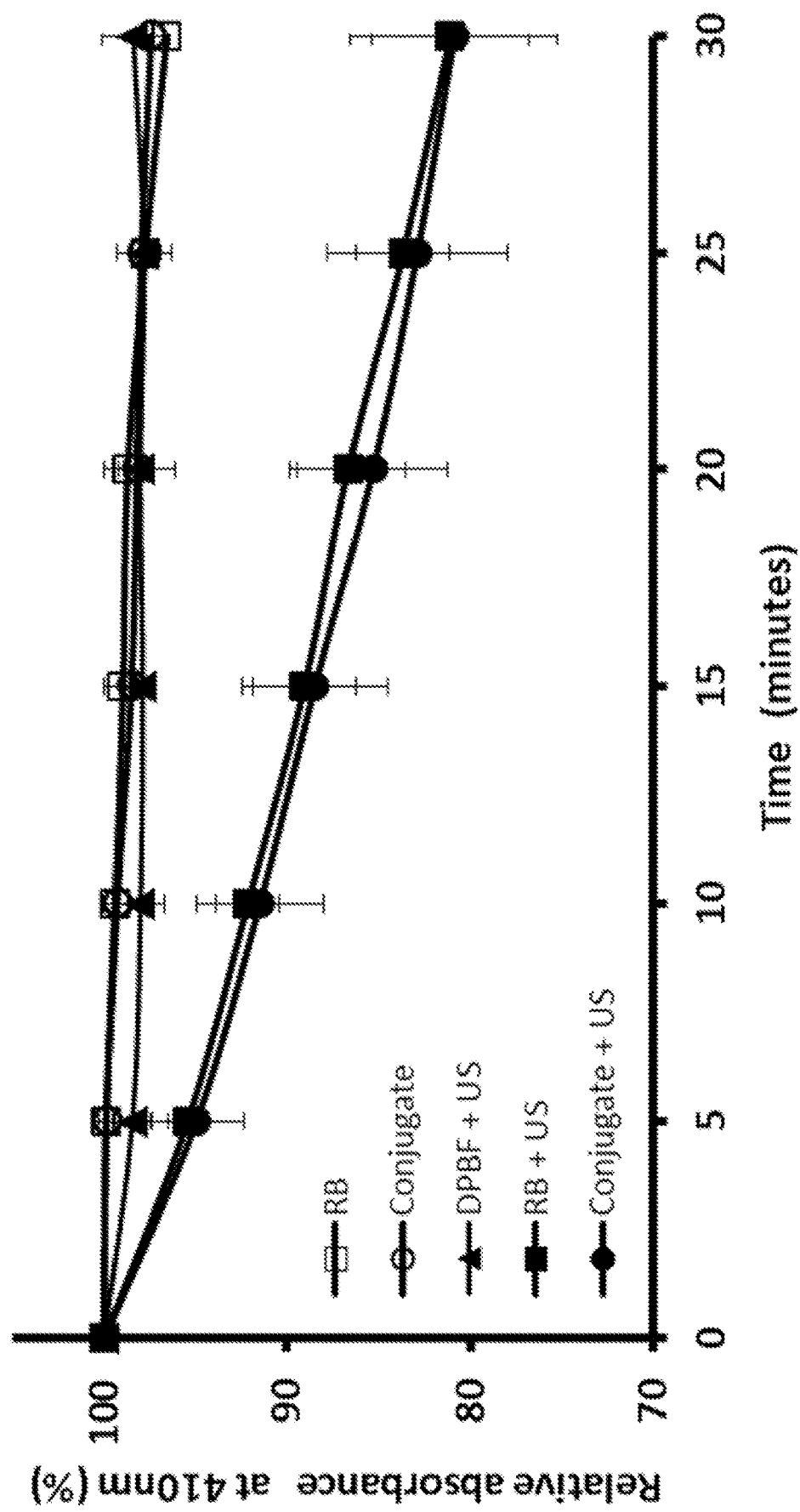
FIG. 2(d) is a chart of 1,3-Diphenylisobenzofuran (DPBF) absorbance at 410 nm against time for solutions containing different substances and with or without ultrasound treatment as indicated by the key on the lower left of the chart. "RB" represents Rose Bengal, "Conjugate" represents a conjugate of Rose Bengal and a peptide having the amino acid sequence defined by SEQ ID NO. 2, "DPBF" represents 1,3-Diphenylisobenzofuran alone, "+US" represents ultrasound treatment.

The Ability of the Rose Bengal-C(KLAKLAK)$_2$ (SEQ ID NO. 2) Conjugate to Generate ROS The ability of the Rose Bengal-C(KLAKLAK)$_2$ (SEQ ID NO. 2) conjugate to generate reactive oxygen species (ROS) upon exposure to low intensity ultrasound was determined using the chromogenic ROS probe 1,3-diphenylisobenzofuran (DPBF). DPBF has an intense absorbance band centred at 410 nm in its native furan form but is readily bleached by ROS to the corresponding di-ketone. This conversion to the di-ketone is accompanied by a loss in absorbance at 410 nm that can be used to determine the amount of ROS produced. An EtOH:H$_2$O (50:50 v/v) (10 mL) solution was prepared containing Rose Bengal or Rose Bengal-C(KLAKLAK)$_2$ (SEQ ID NO. 2) (0.5 µM) and 1,3-diphenylisobenzofuran (DPBF) (20 µM). The solutions were then irradiated for 30 min with ultrasound using a sonoporator (Sonidel SP 100 sonoporator; frequency 1 MHz, power density 3.0 W/cm$^2$, 50% duty cycle, pulse repetition frequency 100 Hz). Aliquots were taken every 5 minutes and the absorbance at 410 nm was recorded using a ultraviolet-visible spectrometer (Cary 50 ultraviolet-visible (UV-Vis) spectrometer). Control experiments in the absence of drug (i.e. DPBF+stimulus) were also performed for comparative purposes (n=3). The results are shown in FIG. 2(d) and show a significant reduction in DPBF absorbance for both Rose Bengal, or Rose Bengal-C(KLAKLAK)$_2$ (SEQ ID NO. 2), treated with ultrasound relative to the controls indicating efficient ROS production in the ultrasonic field. In addition, the almost identical profile observed for both Rose Bengal and Rose Bengal-C(KLAKLAK)$_2$ (SEQ ID NO. 2) suggests the presence of the peptide does not inhibit ultrasound-induced ROS production by the sensitizer.

Example 3

The Effect of PDT Using a Rose Bengal-C(KLAKLAK)$_2$ (SEQ ID NO. 2) Conjugate on B16 Melanoma Cells Murine melanoma B16-F10 Luc-2 cells were maintained Dulbecco's Modified Eagle Media (DMEM) supplemented with 10% foetal bovine serum (FBS) and 1% penicillin streptomycin. The cells were incubated at 37° C. in a humidified 5% (v/v) $CO_2$ atmosphere. Cells were seeded at a concentration of $4×10^3$ cells per well in 96-well tissue culture plate for 24 hours. The medium was removed from each well and the cells incubated for 3 h with drug (100 μL) at concentrations of 2.5 μM, 5.0 μM and 10 μM in media. The drug solution was then removed and selected wells exposed to white light for 1 min (22.8 J/cm$^2$). Fresh media was then added to each of the wells and cell viability determined 24 h later using a MTT assay. Each experiment was repeated on 3 separate occasions with an n=6 on each occasion.

For the bioluminescent assay, imaging was undertaken using a Xenogen IVIS-100 bioluminescence/fluorescence optical imaging system. Treatments were performed as described above. D-Luciferin at 1.5% w/w was then added to treated wells and bioluminescence intensity was quantified 5 min later using the IVIS-100 system and Living Image Software as per protocol (Caliper LifeSciences). Regions of interest (RoI) were drawn around the wells to evaluate the intensity of signal emitted and expressed photons/second (p/s).

The RB-C(KLAKLAK)$_2$ (SEQ ID NO. 2) conjugate (which is a conjugate of Rose Bengal and a peptide having the amino acid sequence defined by SEQ ID NO. 2) effectively killed B16-F10-Luc2 melanoma cells as part of PDT. The RB-C(KLAKLAK)$_2$ (SEQ ID NO. 2) L enantiomer had a more potent cytotoxic effect than the RB-C(KLAKLAK)$_2$ (SEQ ID NO. 2) D enantiomer as part of PDT in this experiment, suggesting that stereochemistry may be a factor.

Figure 3:
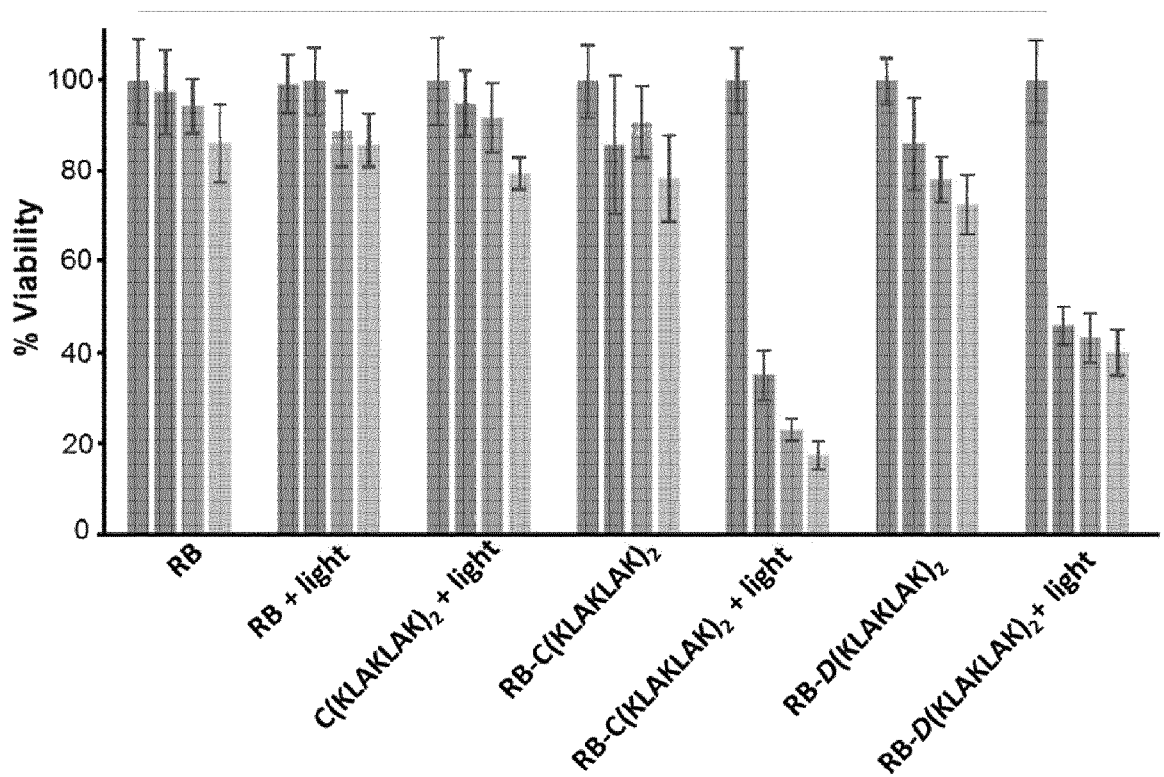
FIG. 3 is a bar chart showing cell viability following treatment as indicated on the x-axis. "RB" represents Rose Bengal, "+light" represents photodynamic therapy, "C(KLAKLAK)$_2$" (SEQ ID NO. 2) represents a peptide having the amino acid sequence defined by SEQ ID NO. 2, "RB-C(KLAKLAK)$_2$" (SEQ ID NO. 2) represents a conjugate of Rose Bengal and a peptide having the amino acid sequence defined by SEQ ID NO. 2, "RB-D(KLAKLAK)$_2$" (SEQ ID NO. 1) represents the all-D enantiomer of a peptide having the amino acid sequence defined by SEQ ID NO. 1. For each treatment group on the x-axis, counting from left, $1^{st}$ column=0 µM concentration, $2^{nd}$ column=2.5 µM concentration; $3^{rd}$ column=5 µM concentration, and 4th column=10 µM concentration. Light conditions used: white light (22.8 J/cm2). These results show photodynamic therapy using the conjugate of Rose Bengal and a peptide having the amino acid sequence defined by SEQ ID NO. 2 was significantly better than photodynamic therapy using Rose Bengal alone, or the conjugate of Rose Bengal and a peptide having the amino acid sequence defined by SEQ ID NO. 2 alone, or a peptide having the amino acid sequence defined by SEQ ID NO. 2+light.
Figure 4:
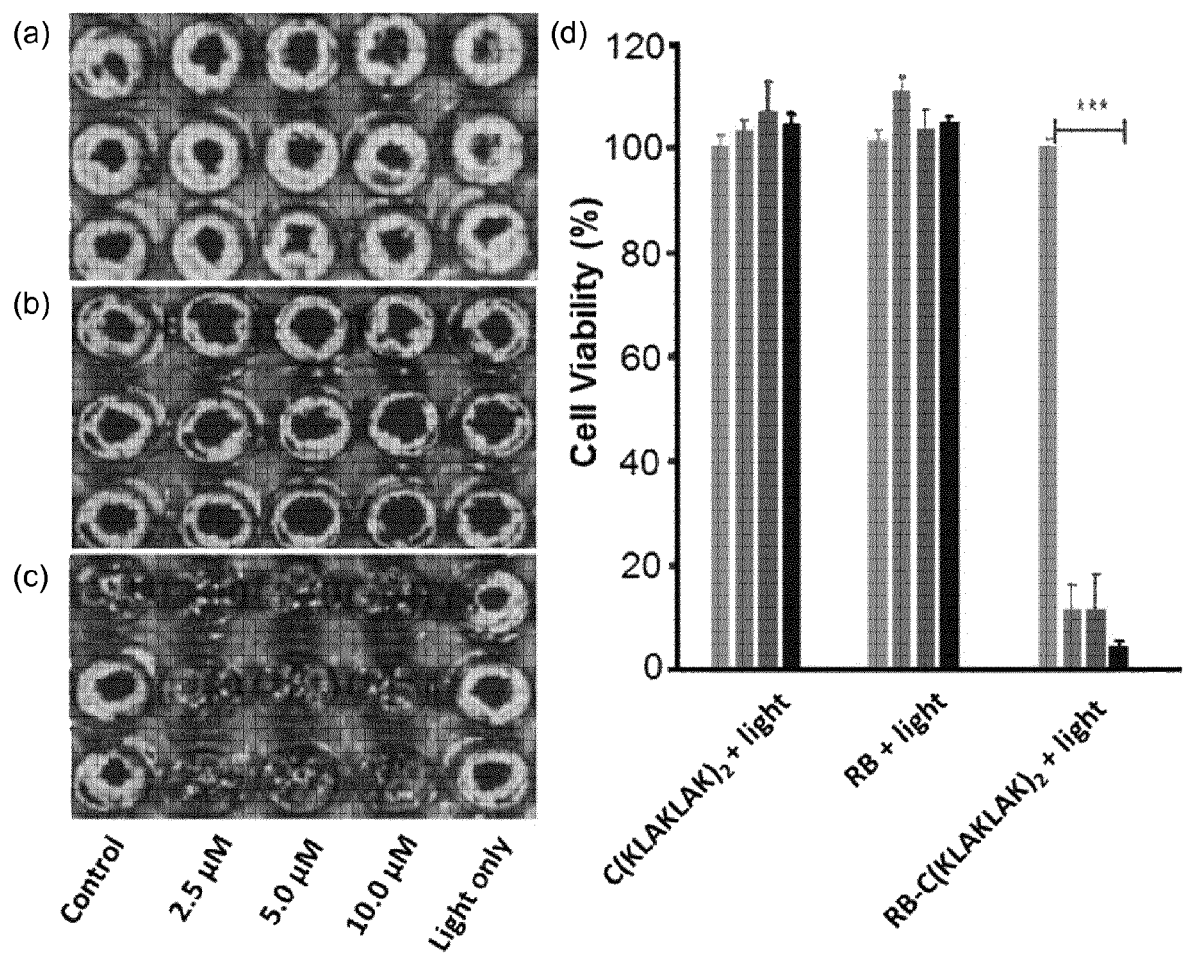
FIGS. 4 (a), (b) and (c) are bioluminescent images of B16-F10-Luc2 melanoma cell cultures in 96-well tissue culture plates. Far left wells were untreated and far right wells treated with light only. The middle three rows were treated with 2.5 µM, 5.0 µM or 10 µM of the treatment listed below, plus light. Cells were treated with either (a) a peptide having the amino acid sequence defined by SEQ ID NO. 2; (b) Rose Bengal; or (c) a conjugate of Rose Bengal and a peptide having the sequence defined by SEQ ID NO. 2. The light conditions used were: white light (22.8 J/cm$^2$).

These results are presented in FIG. 3.

Example 4

The Effect of SDT Using a Rose Bengal-C(KLAKLAK)$_2$ (SEQ ID NO. 2) Conjugate on B16 Melanoma Cells Murine melanoma B16-F10 Luc-2 cells were maintained Dulbecco's Modified Eagle Media (DMEM) supplemented with 10% foetal bovine serum (FBS) and 1% penicillin streptomycin. The cells were incubated at 37° C. in a humidified 5% (v/v) $CO_2$ atmosphere. Cells were seeded at a concentration of $4×10^3$ cells per well in 96-well tissue culture plate for 24 hours. The medium was removed from each well and the cells incubated for 3 hours with drug (100 μL) at concentrations of 2.5 μM, 5.0 μM and 10 μM in media. The drug solution was then removed and selected wells exposed to white light for 1 min (22.8 J/cm$^2$). Fresh media was then added to each of the wells and cell viability determined 24 hours later using a MTT assay (a colorimetric assay). Each experiment was repeated on 3 separate occasions with an n=6 on each occasion.

For the bioluminescent assay, imaging was undertaken using a Xenogen IVIS-100 bioluminescence/fluorescence optical imaging system. Treatments were performed as described above. D-Luciferin at 1.5% w/w was then added to treated wells and bioluminescence intensity was quantified 5 minutes later using a small animal in vivo imaging system (IVIS-100 system) and image analysis software (Living Image Software; Caliper LifeSciences) as per the manufacturer's protocol. Regions of interest (RoI) were drawn around the wells to evaluate the intensity of signal emitted and expressed photons/second (p/s).

The RB-C(KLAKLAK)$_2$ (SEQ ID NO. 2) conjugate (which is a conjugate of Rose Bengal and a peptide having the amino acid sequence defined by SEQ ID NO. 2) effectively killed B16-F10-Luc2 melanoma cells as part of SDT.

Figure 5:
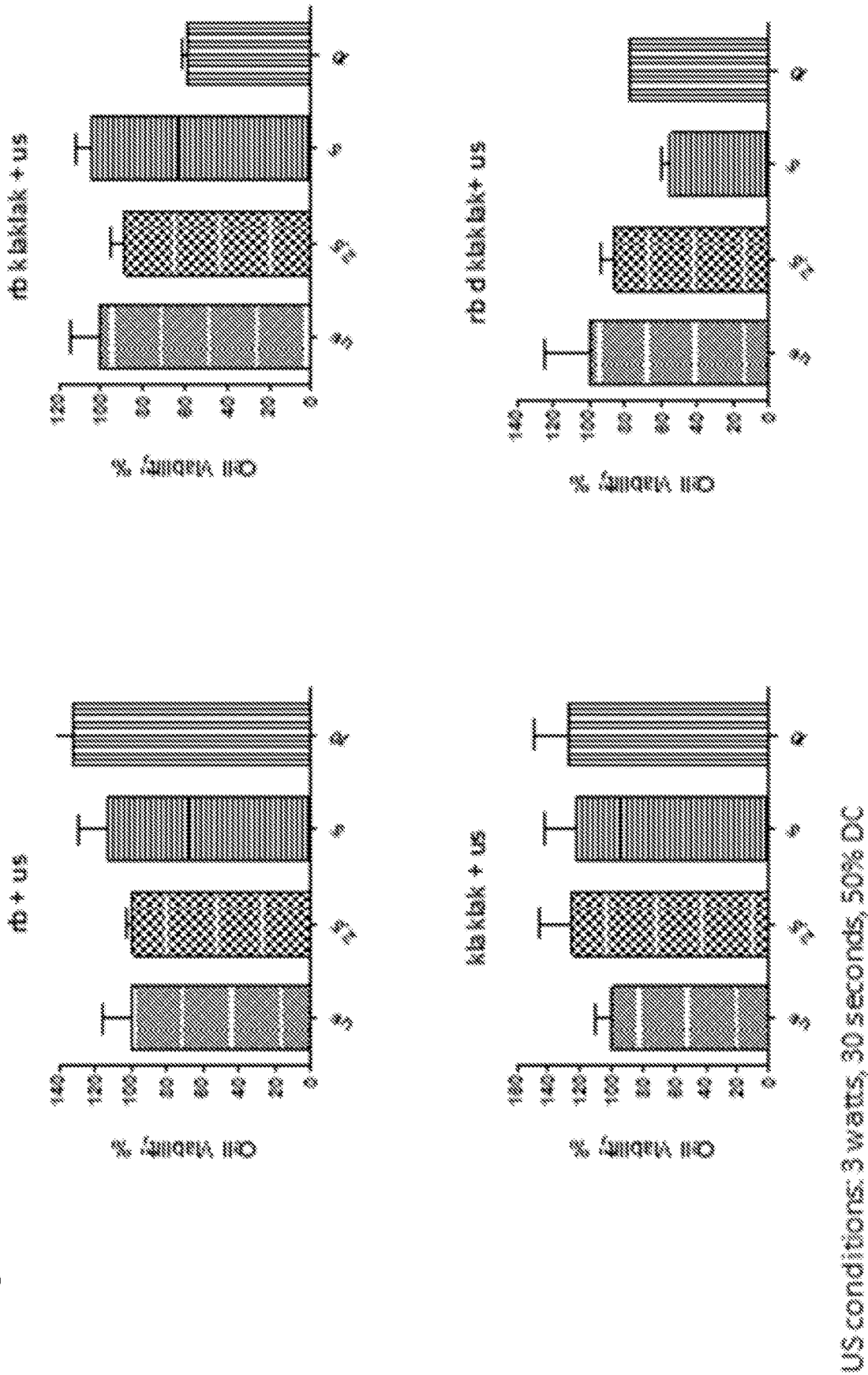
FIG. 5 shows landscape-oriented bar charts representing MTT B16-F10-Luc2 melanoma cell viability assay results, wherein "rb" represents Rose Bengal; "+us" represents sonodynamic therapy; "klaklak" (SEQ ID NO. 5) represents a peptide having the amino acid sequence defined by SEQ ID NO. 2; "rb klaklak" (SEQ ID NO. 5) represents a conjugate of Rose Bengal and a peptide having the amino acid sequence defined by SEQ ID NO. 2 wherein all chiral amino acids are the L-enantiomer; "rb d klaklak" (SEQ ID NO. 5) represents a conjugate of Rose Bengal and a peptide having the amino acid sequence defined by SEQ ID NO. 2 wherein all chiral amino acids are the D-enantiomer; "US conditions" represents ultrasound conditions; and "DC" represents duty cycle.

These results are presented in FIG. 5.

Example 5

Effect of PDT Using a Rose Bengal-(KLAKLAK)$_2$ (SEQ ID NO. 1) Conjugate on B16 Melanoma Tumour Growth in a Mouse Model In these studies all animals were treated humanely and in accordance with licensed procedures under the UK Animals (Scientific Procedures) Act 1986. B16-F10-Luc2 cells ($3×10^5$) maintained as described in Example 3, were re-suspended in 100 μL of PBS and implanted into the rear dorsum of SCID mice. Four days after implantation tumour measurements were taken using calipers and tumour volume calculated from the geometric mean diameter using the equation: tumour volume=$4πR^3/3$. The animals were then randomly distributed into four groups (n=5): Group 1 involved untreated animals; Group 2 treated with the RB-(KLAKLAK)$_2$ (SEQ ID NO. 1) conjugate and no light; Group 3 treated with the RB-(KLAKLAK)$_2$ (SEQ ID NO. 1) conjugate and light; Group 4 treated with RB and light. Following induction of anaesthesia (intraperitoneal injection of Hypnorm/Hypnovel), a 100 μL aliquot of PBS containing 100 μM RB or the RB-(KLAKLAK)$_2$ (SEQ ID NO. 1) conjugate was administered by tail vein injection. Group 3 and Group 4: 30 minutes later tumours were exposed to white light for 3 min (68.4 J/cm$^{-2}$). After treatment, animals were allowed to recover from anaesthesia and tumour volume was monitored for 12 days with animals retreated using the same conditions on days 1, 2, 7 and 9. The % increase in tumour volume was calculated employing the pre-treatment measurements for each group. On day 13, the animals were euthanized and the tumours were removed for analysis.

The RB-C(KLAKLAK)$_2$ (SEQ ID NO. 2) conjugate (which is a conjugate of Rose Bengal and a peptide having the amino acid sequence defined by SEQ ID NO. 2) effectively reduced B16-F10-Luc2 melanoma tumour growth in mice as part of PDT or SDT. Use of the RB-C(KLAKLAK)$_2$ (SEQ ID NO. 2) conjugate as part of PDT inhibited tumour growth to a greater extent than use of the RB-C(KLAKLAK)$_2$ (SEQ ID NO. 2) conjugate as part of SDT in this experiment.

Figure 6:
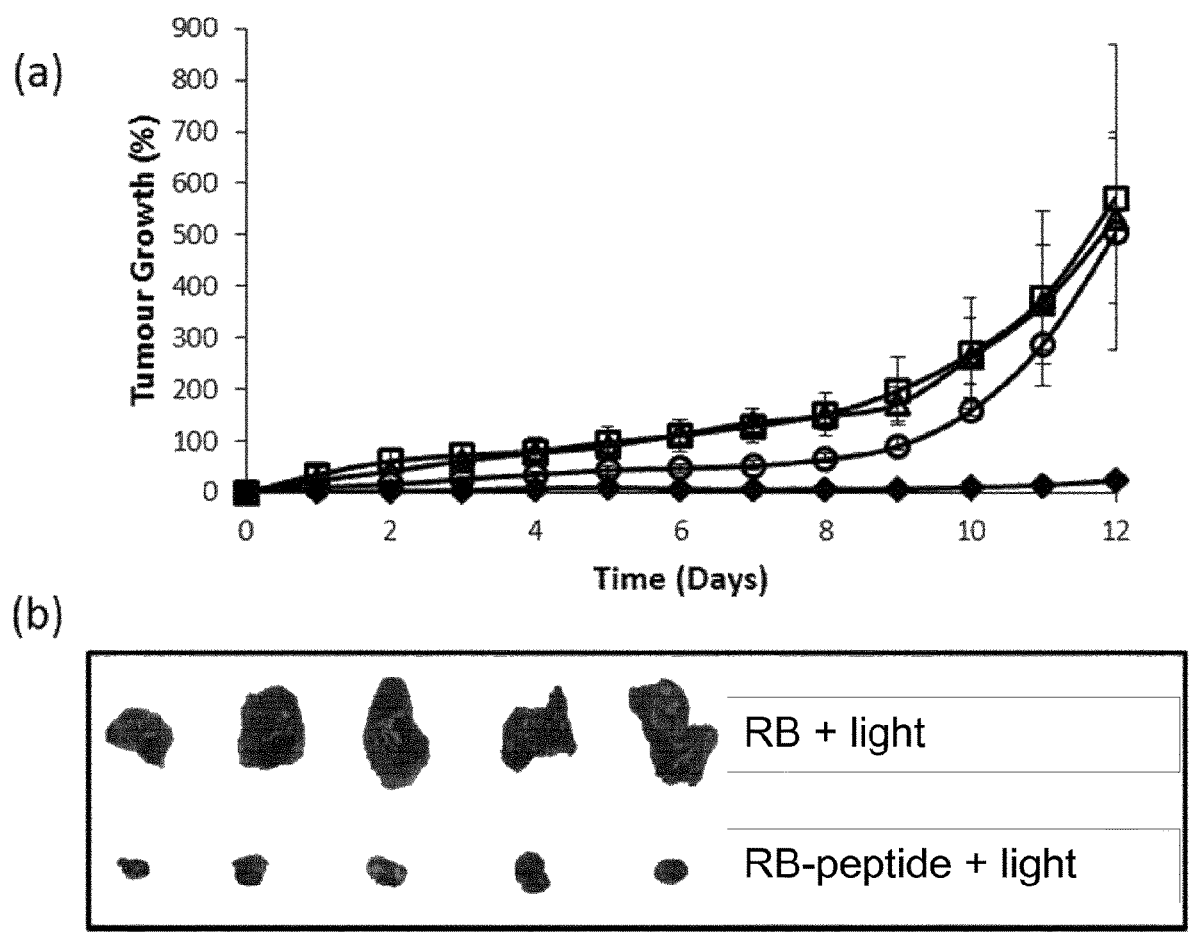
FIG. 6(a) is a chart of tumour growth as a function of time for animals bearing orthotopic B16-Luc tumours and exposed to (i) no treatment (open squares) (ii) a conjugate of Rose Bengal and a peptide having the amino acid sequence defined by SEQ ID NO. 2 alone (open triangles) (iii) photodynamic therapy using Rose Bengal (open circles) and (iv) photodynamic therapy using a conjugate of Rose Bengal and a peptide having the amino acid sequence defined by SEQ ID NO. 2 (filled diamonds).
FIG. 6(b) shows photographs of tumours excised 13 days following initial photodynamic therapy treatment using Rose Bengal (top) compared to photodynamic therapy treatment using a conjugate of Rose Bengal and a peptide having the amino acid sequence defined by SEQ ID NO. 2 (bottom). Results reveal significant reduction in tumour size for animals that underwent photodynamic therapy treatment using the a conjugate of Rose Bengal and a peptide having the amino acid sequence defined by SEQ ID NO. 2 relative to photodynamic therapy using Rose Bengal alone or the effect of the a conjugate of Rose Bengal and a peptide having the amino acid sequence defined by SEQ ID NO. 2 in the absence of light.

These results are presented in FIG. 6.

Example 6

PDT and SDT Treatment of Ectopic B16 Melanoma Tumours in SCID Mice Using the Rose Bengal-(KLAKLAK)$_2$ (SEQ ID NO. 1) Conjugate B16-F10-Luc2 cells ($3×10^5$) maintained as described in Example 3, were re-suspended in 100 μL of PBS and implanted into the rear dorsum of SCID mice. Four days after implantation tumour measurements were taken using calipers and tumour volume calculated from the geometric mean diameter using the equation: tumour volume=$4πR^3/3$. The animals were then randomly distributed into four groups (n=5): Group 1 involved untreated animals; Group 2 treated with the RB-(KLAKLAK)$_2$ (SEQ ID NO. 1) conjugate and no light; Group 3 treated with the RB-(KLAKLAK)$_2$ (SEQ ID NO. 1) conjugate and light; Group 4 treated with the RB-(KLAKLAK)$_2$ (SEQ ID NO. 1) conjugate and SDT, and Group 5 treated with RB and light. Following induction of anaesthesia (intraperitoneal injection of Hypnorm/Hypnovel), a 100 µL aliquot of PBS containing 100 µM RB or the RB-(KLAKLAK)$_2$ (SEQ ID NO. 1) conjugate was administered by tail vein injection. Group 3 and Group 5: 30 minutes later tumours were exposed to white light for 3 min (68.4 J/cm$^{-2}$). Group 4: on the same day tumours were exposed to ultrasound for 3.5 min (power: 3 W cm-2; Frequency 1 MHz; Duty cycle=30%; Pulse repetition 100 Hz). After treatment, animals were allowed to recover from anaesthesia and tumour volume was monitored for 12 days with animals retreated using the same conditions on days 1, 2, 7 and 9. The % increase in tumour volume was calculated employing the pre-treatment measurements for each group. On day 13, the animals were euthanized and the tumours were removed for analysis.

The RB-(KLAKLAK)$_2$ (SEQ ID NO. 1) conjugate (which is a conjugate of Rose Bengal and a peptide having the amino acid sequence defined by SEQ ID NO. 1) effectively reduced B16-F10-Luc2 melanoma tumour growth in mice as part of PDT and SDT, although PDT was superior using this model system.

Figure 7:
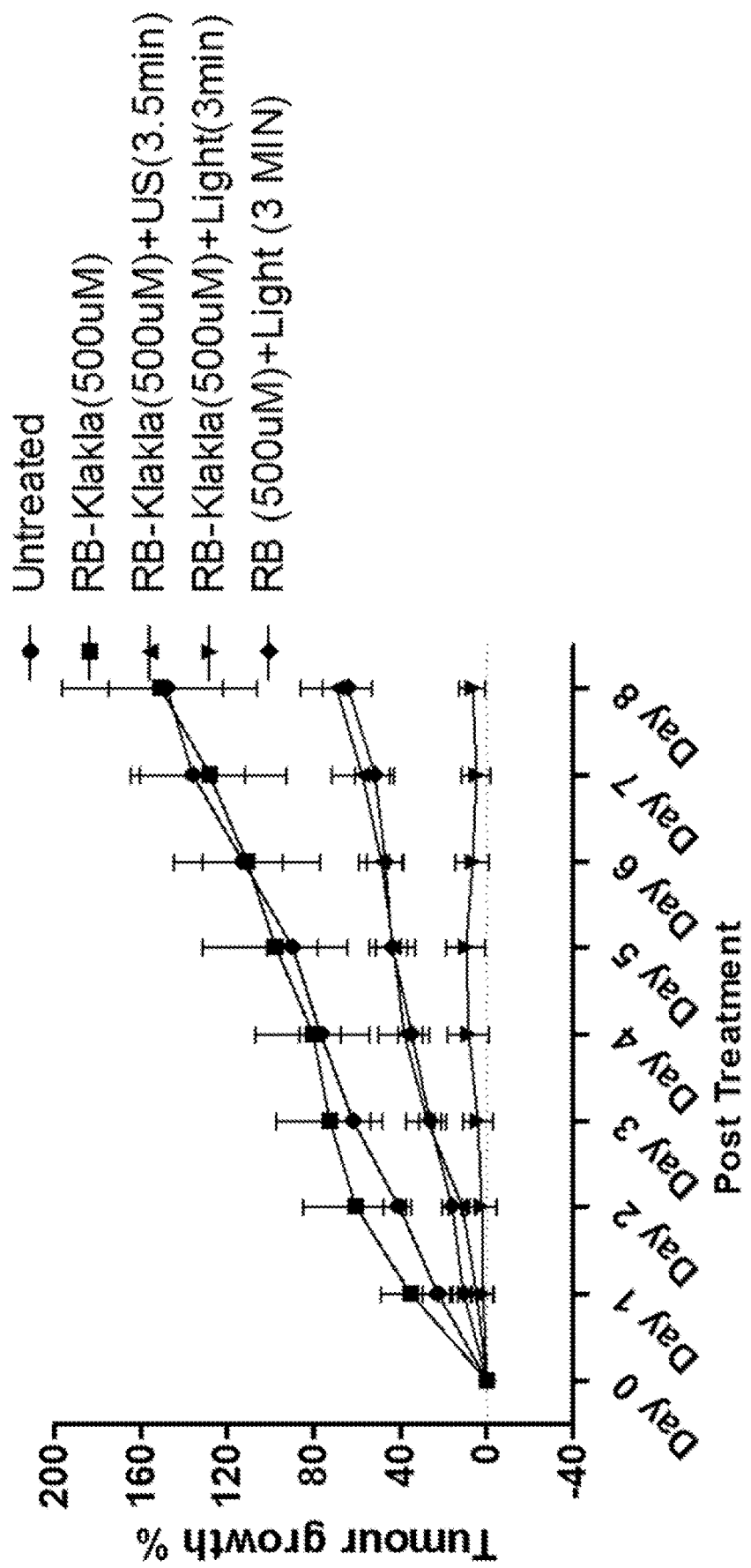
FIG. 7 is a landscape-oriented line chart representing tumour growth as a percentage of the initial tumour size, over 8 days following treatment, for four different treatment groups and an untreated control; wherein "RB-Klaklak" (SEQ ID NO. 5) represents a conjugate of Rose Bengal and a peptide having the amino acid sequence defined by SEQ ID NO. 2; "+US" represents sonodynamic therapy; "+Light" represents photodynamic therapy; and "RB" represents Rose Bengal.

These results are presented in FIG. 7.

Example 7

The Effect of PDT Using a Rose Bengal-C(KLAK-LAK)$_2$ (SEQ ID NO. 2) Conjugate or a Rose Bengal-C(KLAKLAK) (SEQ ID NO. 6) Conjugate on MCF-7 Breast Cancer Cells Human MCF-7 invasive breast ductal carcinoma cells were maintained Dulbecco's Modified Eagle Media (DMEM) supplemented with 10% foetal bovine serum (FBS) and 1% penicillin streptomycin. The cells were incubated at 37° C. in a humidified 5% (v/v) $CO_2$ atmosphere. Cells were seeded at a concentration of 5×10$^3$ cells per well in 96-well tissue culture plate for 24 hours. The medium was removed from each well and the cells incubated for 3 h with drug (100 µL) at concentrations of 0.05 µM, 0.1 µM, 0.5 µM and 1 µM in media. The drug solution was then removed and the cells washed twice with PBS, fresh media was added and selected wells exposed to white light for 1 min (22.8 J/cm$^2$). Fresh media was then added to each of the wells and cell viability determined 24 h later using a MTT assay. Each experiment was repeated on 3 separate occasions with an n=6 on each occasion.

The RB-C(KLAKLAK)$_2$ (SEQ ID NO. 2) conjugate (which is a conjugate of Rose Bengal and a peptide having the amino acid sequence defined by SEQ ID NO. 2) and the RB-C(KLAKLAK) (SEQ ID NO. 6) conjugate (which is a conjugate of Rose Bengal and a peptide having the amino acid sequence defined by SEQ ID NO. 6) effectively killed MCF-7 invasive breast ductal carcinoma cells as part of PDT.

Figure 8:
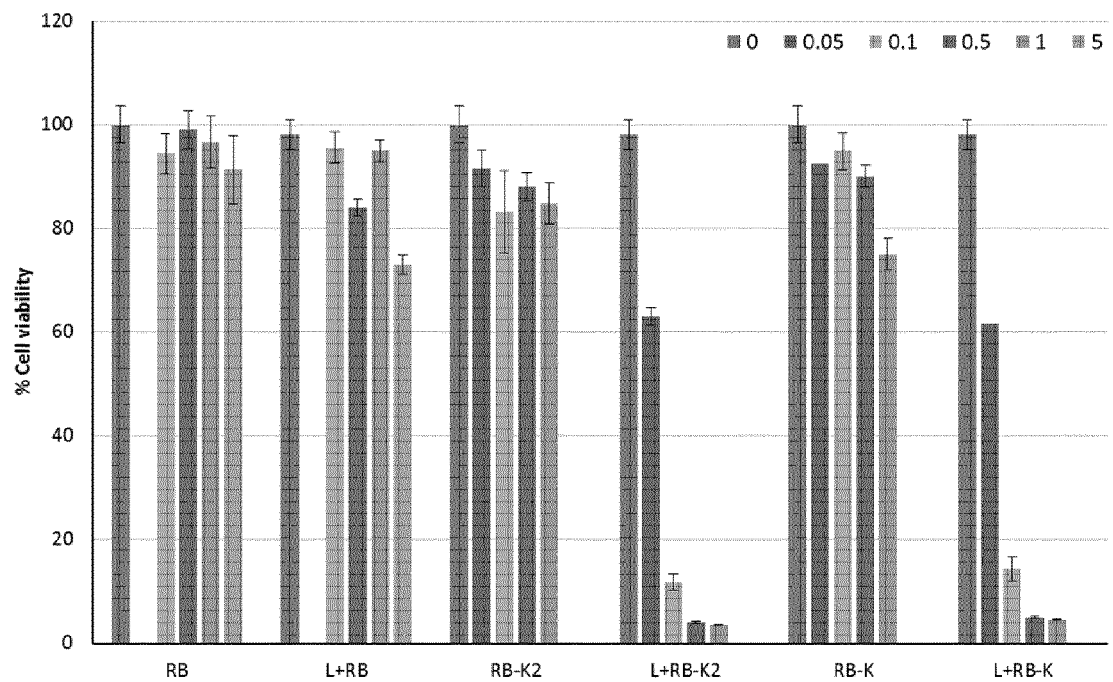
FIG. 8 is a bar chart showing cell viability for breast cancer MCF-7 cells treated with either (i) Rose Bengal (RB) (ii) Rose Bengal+light (L+RB) (iii) Rose Bengal-C(KLAKLAK)2 (SEQ ID NO. 2) (RB-K2) (iv) Rose Bengal-C(KLAKLAK)2 (SEQ ID NO. 2)+light (L+RB-K2) (v) Rose Bengal-CKLAKLAK (SEQ ID NO. 6) (RB-K) (vi) Rose Bengal-CKLAKLAK (SEQ ID NO. 6)+Light (L+RB-K), wherein different bars reflect different concentrations (µM) as depicted in the figure inset.

These results are presented in FIG. 8.

Example 8

The Effect of PDT Using a Rose Bengal-C(KLAK-LAK)$_2$ (SEQ ID NO. 2) Conjugate or a Rose Bengal-C(KLAKLAK) (SEQ ID NO. 6) Conjugate on PANC-1 Pancreatic Cancer Cells Human PANC-1 epithelioid carcinoma cells were maintained Dulbecco's Modified Eagle Media (DMEM) supplemented with 10% foetal bovine serum (FBS) and 1% penicillin streptomycin. The cells were incubated at 37° C. in a humidified 5% (v/v) $CO_2$ atmosphere. Cells were seeded at a concentration of 5×10$^3$ cells per well in 96-well tissue culture plate for 24 hours. The medium was removed from each well and the cells incubated for 3 h with drug (100 µL) at concentrations of 0.05 µM, 0.1 µM, 0.5 µM and 1 µM in media. The drug solution was then removed and the cells washed twice with PBS, fresh media was added and selected wells exposed to white light for 1 min (22.8 J/cm$^2$). Fresh media was then added to each of the wells and cell viability determined 24 h later using a MTT assay. Each experiment was repeated on 3 separate occasions with an n=6 on each occasion.

The RB-C(KLAKLAK)$_2$ (SEQ ID NO. 2) conjugate (which is a conjugate of Rose Bengal and a peptide having the amino acid sequence defined by SEQ ID NO. 2) and the RB-C(KLAKLAK) (SEQ ID NO. 6) conjugate (which is a conjugate of Rose Bengal and a peptide having the amino acid sequence defined by SEQ ID NO. 6) effectively killed PANC-1 epithelioid carcinoma cells as part of PDT.

Figure 9:
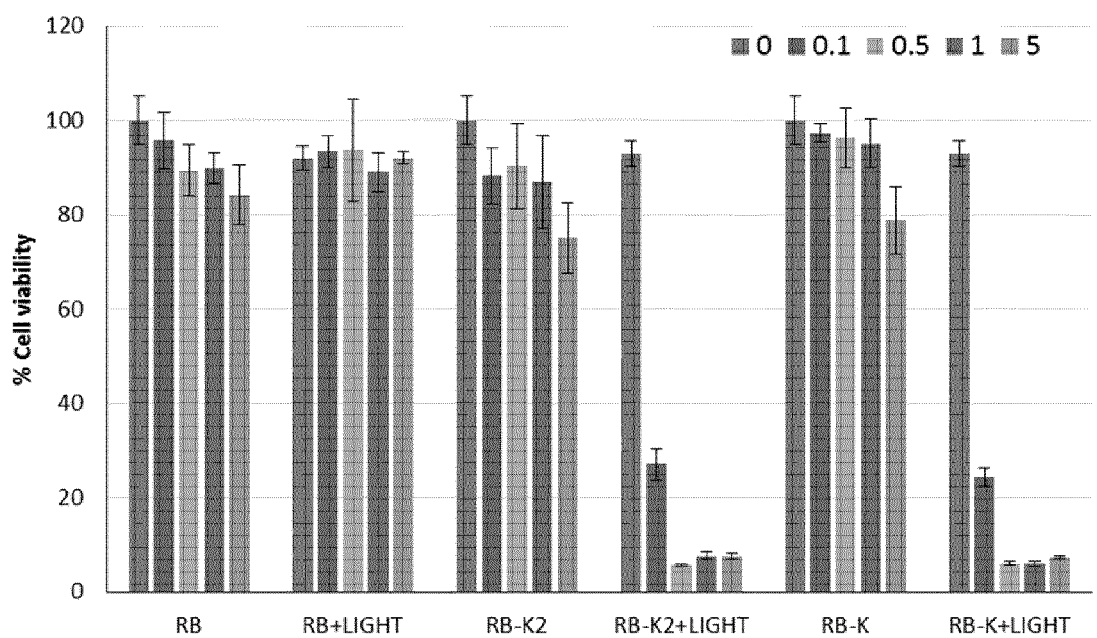
FIG. 9 is a bar chart showing cell viability for pancreatic cancer Panc-01 cells treated with either (i) Rose Bengal (RB) (ii) Rose Bengal+light (L+RB) (iii) Rose Bengal-C(KLAKLAK)2 (SEQ ID NO. 2) (RB-K2) (iv) Rose Bengal-C(KLAKLAK)2 (SEQ ID NO. 2)+light (L+RB-K2) (v) Rose Bengal-CKLAKLAK (SEQ ID NO. 6) (RB-K) (vi) Rose Bengal-CKLAKLAK (SEQ ID NO. 6)+Light (L+RB-K), wherein different bars reflect different concentrations (µM) as depicted in the figure inset.
Figure 10:
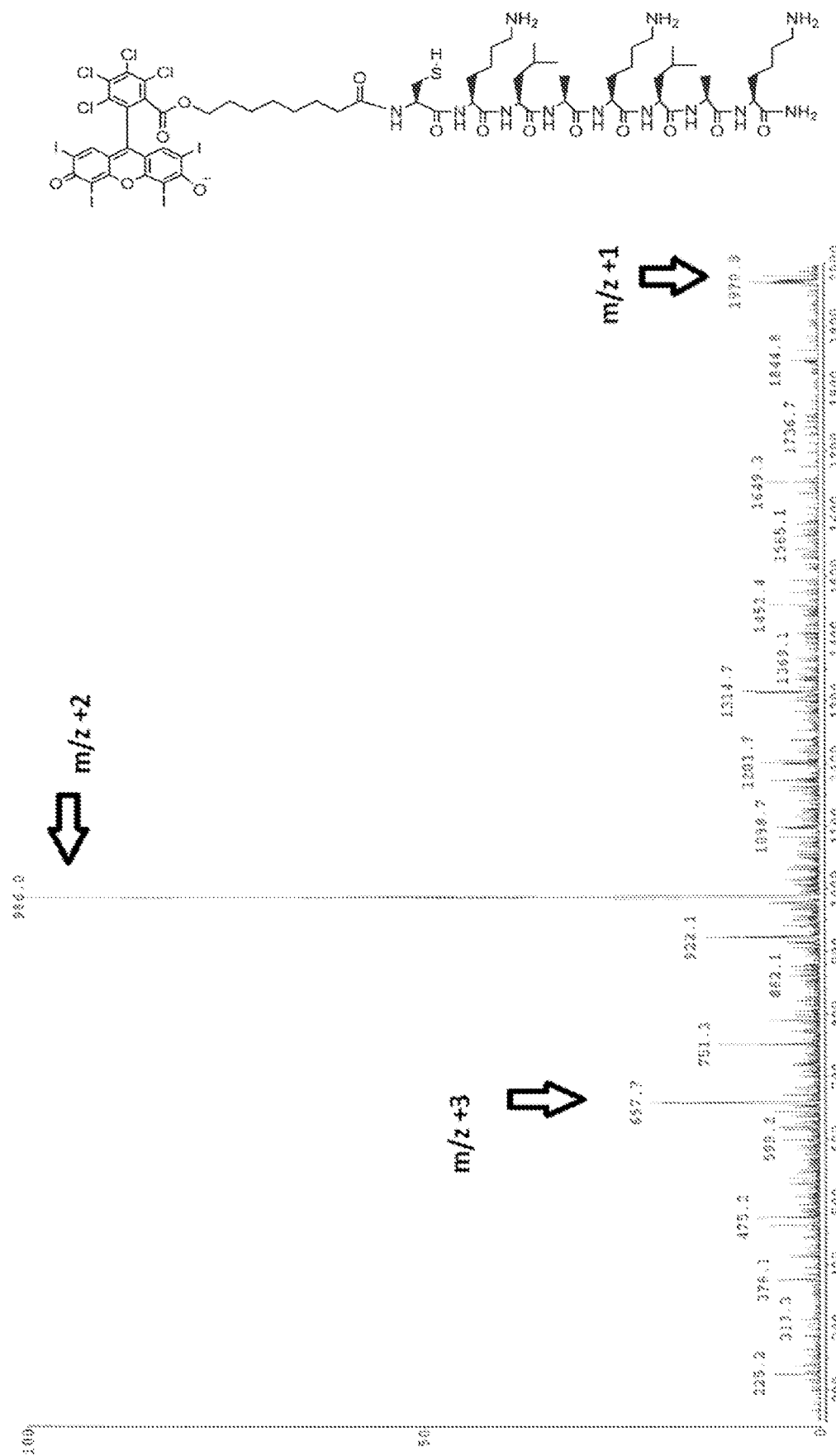
FIG. 10 depicts the structure of RB-CKLAKLAK (SEQ ID NO. 6) (top) and positive electrospray mass spectrum of the RB-CKLAKLAK (SEQ ID NO. 6) (bottom).

These results are presented in FIG. 9.

REFERENCES

Costley, D., Nesbitt, H., Ternan, N., Dooley, J., Huang, Y. Y., Hamblin, M. R., McHale A. P., & Callan, J. F. (2017). Sonodynamic inactivation of Gram-positive and Gram-negative bacteria using a Rose Bengal-antimicrobial peptide conjugate. International Journal of Antimicrobial Agents.

Fowley C, Nomikou N, McHale A P, McCarron P A, McCaughan B, Callan J F. Water soluble quantum dots as hydrophilic carriers and two-photon excited energy donors in photodynamic therapy. J Mater Chem 2012; 22,6456-62.

The invention claimed is:

1. A method for the treatment of cancer in a subject in need thereof; the method comprising the step of administering a sensitizer-peptide conjugate comprising at least one sensitizer and at least one peptide to the subject, wherein the at least one sensitizer comprises Rose Bengal; and wherein the at least one peptide comprises a sequence selected from the group consisting of: SEQ ID NO: 1, SEQ ID NO: 2, SEQ ID NO: 3, SEQ ID NO: 4, SEQ ID NO: 5, and SEQ ID NO: 6.

2. The method according to claim 1; wherein the at least one peptide comprises the amino acid sequence defined by SEQ ID NO. 6.

3. The method according to claim 1; wherein the at least one peptide comprises the amino acid sequence defined by SEQ ID NO. 2.

4. The method according to claim 1; wherein the sensitizer-peptide conjugate further comprises at least one linker between the at least one sensitizer and the at least one peptide.

5. The method according to claim 4; wherein the at least one linker comprises one or more polymers.

6. The method according to claim 4; wherein the at least one linker comprises the general formula —COOCH$_2$CH$_2$CH$_2$CH$_2$CH$_2$CH$_2$CH$_2$CO—.

7. The method according to claim 1; wherein the peptide comprises at least one chiral amino acid; wherein the at least one chiral amino acid is the L enantiomer.

8. The method according to claim 1; wherein the sensitizer-peptide conjugate is activated by a trigger.

9. The method according to claim 8; wherein the trigger is electromagnetic radiation.

10. The method according to claim 9; wherein the method is part of photodynamic therapy.

11. The method according to claim 8; wherein the trigger is sound.

12. The method according to claim 11; wherein the method is part of sonodynamic therapy.

13. The method according to claim 1; wherein the cancer is selected from the group consisting of breast cancer, pancreatic cancer, skin cancer, head and neck cancer, oesophageal cancer, bladder cancer, and prostate cancer.

\* \* \* \* \*